(12) United States Patent
  Masters et al.

(10) Patent No.: US 9,107,937 B2
(45) Date of Patent: *Aug. 18, 2015

(54) WOUND TREATMENTS WITH CROSSLINKED PROTEIN AMORPHOUS BIOMATERIALS

(75) Inventors: David B. Masters, Minneapolis, MN (US); Eric P. Berg, Plymouth, MN (US)

(73) Assignee: Gel-Del Technologies, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/435,839

(22) Filed: Mar. 30, 2012

(65) Prior Publication Data
US 2012/0282300 A1  Nov. 8, 2012

Related U.S. Application Data

(63) Continuation of application No. 10/929,117, filed on Aug. 26, 2004, now Pat. No. 8,153,591.

(60) Provisional application No. 60/497,824, filed on Aug. 26, 2003.

(51) Int. Cl.
  *A61K 31/726* (2006.01)
  *A61K 31/727* (2006.01)
  (Continued)

(52) U.S. Cl.
  CPC .............. *A61K 31/715* (2013.01); *A61K 8/64* (2013.01); *A61K 8/65* (2013.01); *A61K 31/70* (2013.01); *A61K 31/726* (2013.01); *A61K 31/727* (2013.01); *A61K 31/728* (2013.01); *A61K 35/545* (2013.01); *A61K 38/39* (2013.01); *A61K 45/06* (2013.01); *A61L 27/20* (2013.01);
  (Continued)

(58) Field of Classification Search
  CPC ......... A61K 8/64; A61K 8/65; A61K 31/726; A61K 31/727; A61K 31/728
  See application file for complete search history.

(56) References Cited

U.S. PATENT DOCUMENTS 3,996,934 A   12/1976  Zaffaroni
4,060,081 A   11/1977  Yannas et al.
(Continued)

FOREIGN PATENT DOCUMENTS

CA   1071814 A  *  2/1980
CA   1 239 755      8/1988
(Continued)

OTHER PUBLICATIONS

Veves et al.; "A Randomized, Controlled Trial of Promogran (a Collagen/Oxidized Regenerated Cellulose Dressing) vs Standard Treatment in the Management of Diabetic Foot Ulcers"; Arch Surg.; Jul. 2002; 137:822-827.*

(Continued)

*Primary Examiner* — Timothy Thomas
(74) *Attorney, Agent, or Firm* — Patterson Thuente Pedersen, P.A.

(57) ABSTRACT

Biomaterials and the related methods of making and using biomaterials for wound treatment. The biomaterial defines an amorphous material that is crosslinked with one or more crosslinking agents an includes aggregated complexes having homogenously distributed biocoacervated components. The biocoacervated components include one or more soluble or solubilized primary proteins combined with one or more glycosaminoglycans and one or more biocompatible solvents. The biomaterial can be utilized by administering the biomaterial to a wound.

12 Claims, 25 Drawing Sheets

(51) Int. Cl.

| | | |
|---|---|---|
| A61K 31/728 | (2006.01) | |
| A61K 31/715 | (2006.01) | |
| A61K 8/64 | (2006.01) | |
| A61K 8/65 | (2006.01) | |
| A61K 31/70 | (2006.01) | |
| A61K 35/545 | (2015.01) | |
| A61K 38/39 | (2006.01) | |
| A61K 45/06 | (2006.01) | |
| A61L 27/20 | (2006.01) | |
| A61L 27/22 | (2006.01) | |
| A61L 27/34 | (2006.01) | |
| A61L 27/48 | (2006.01) | |
| A61L 27/50 | (2006.01) | |
| A61L 31/10 | (2006.01) | |
| A61L 33/12 | (2006.01) | |
| A61Q 19/08 | (2006.01) | |
| A61M 25/00 | (2006.01) | |
| A61K 38/00 | (2006.01) | |

(52) U.S. Cl.
CPC .............. *A61L27/22* (2013.01); *A61L 27/34* (2013.01); *A61L 27/48* (2013.01); *A61L 27/507* (2013.01); *A61L 31/10* (2013.01); *A61L 33/12* (2013.01); *A61Q 19/08* (2013.01); *A61K 38/00* (2013.01); *A61K 2800/91* (2013.01); *A61M 25/0045* (2013.01)

(56) References Cited

U.S. PATENT DOCUMENTS

| | | | |
|---|---|---|---|
| 4,226,848 | A | 10/1980 | Nagai et al. |
| 4,250,163 | A | 2/1981 | Nagai et al. |
| 4,252,759 | A | 2/1981 | Yannas et al. |
| 4,280,954 | A | 7/1981 | Yannas et al. |
| 4,286,592 | A | 9/1981 | Chandrasekaran |
| 4,292,299 | A | 9/1981 | Suzuki et al. |
| 4,347,234 | A | 8/1982 | Wahlig et al. |
| 4,350,629 | A | 9/1982 | Yannas et al. |
| 4,394,370 | A | 7/1983 | Jefferies |
| 4,418,691 | A | 12/1983 | Yannas et al. |
| 4,438,253 | A | 3/1984 | Casey et al. |
| 4,448,718 | A | 5/1984 | Yannas et al. |
| 4,458,678 | A | 7/1984 | Yannas et al. |
| 4,474,752 | A | 10/1984 | Haslam et al. |
| 4,505,266 | A | 3/1985 | Yannas et al. |
| 4,517,173 | A | 5/1985 | Kizawa et al. |
| 4,518,721 | A | 5/1985 | Dhabhar et al. |
| 4,522,753 | A | 6/1985 | Yannas et al. |
| 4,526,938 | A | 7/1985 | Churchill et al. |
| 4,553,545 | A | 11/1985 | Maass et al. |
| 4,572,832 | A | 2/1986 | Kigasawa et al. |
| 4,600,533 | A | 7/1986 | Chu |
| 4,652,441 | A | 3/1987 | Okada et al. |
| 4,713,243 | A | 12/1987 | Schiraldi et al. |
| 4,733,665 | A | 3/1988 | Palmaz |
| 4,739,762 | A | 4/1988 | Palmaz |
| 4,780,450 | A | 10/1988 | Sauk et al. |
| 4,787,900 | A | 11/1988 | Yannas |
| 4,800,882 | A | 1/1989 | Gianturco |
| 4,801,299 | A | 1/1989 | Brendel et al. |
| 4,849,141 | A | 7/1989 | Fujioka et al. |
| 4,894,232 | A | 1/1990 | Reiil et al. |
| 4,900,554 | A | 2/1990 | Yanagibashi et al. |
| 4,902,289 | A | 2/1990 | Yannas |
| 4,907,336 | A | 3/1990 | Gianturco |
| 4,915,948 | A | 4/1990 | Gallopo et al. |
| 4,917,161 | A | 4/1990 | Townend |
| 4,947,840 | A | 8/1990 | Yannas et al. |
| 4,955,893 | A | 9/1990 | Yannas et al. |
| 4,959,217 | A | 9/1990 | Sanders et al. |
| 5,035,706 | A | 7/1991 | Giantureo et al. |
| 5,037,392 | A | 8/1991 | Hillstead |
| 5,041,126 | A | 8/1991 | Gianturco |
| 5,041,292 | A | 8/1991 | Feijen |
| 5,100,669 | A | 3/1992 | Hyon et al. |
| 5,102,417 | A | 4/1992 | Palmaz |
| 5,137,729 | A | 8/1992 | Kuroya et al. |
| 5,147,385 | A | 9/1992 | Beck et al. |
| 5,166,187 | A | 11/1992 | Collombel et al. |
| 5,188,837 | A | 2/1993 | Domb |
| 5,192,802 | A | 3/1993 | Rencher |
| 5,282,824 | A | 2/1994 | Gianturco |
| 5,298,258 | A | 3/1994 | Akemi et al. |
| 5,314,915 | A | 5/1994 | Rencher |
| 5,316,023 | A | 5/1994 | Palmaz et al. |
| 5,324,775 | A | 6/1994 | Rhee et al. |
| 5,330,768 | A | 7/1994 | Park et al. |
| 5,423,739 | A | 6/1995 | Phipps et al. |
| 5,443,483 | A | 8/1995 | Kirsch |
| 5,447,940 | A | 9/1995 | Harvey et al. |
| 5,489,304 | A | 2/1996 | Orgill et al. |
| 5,512,291 | A | 4/1996 | Li |
| 5,573,934 | A | 11/1996 | Hubbell et al. |
| 5,591,224 | A | 1/1997 | Schwartz et al. |
| 5,607,445 | A | 3/1997 | Summers |
| 5,642,749 | A | 7/1997 | Perryman |
| 5,665,428 | A | 9/1997 | Cha et al. |
| 5,676,669 | A | 10/1997 | Colvard |
| 5,676,699 | A | 10/1997 | Gogolewski et al. |
| 5,700,478 | A | 12/1997 | Biegajski et al. |
| 5,709,683 | A | 1/1998 | Bagby |
| 5,716,411 | A | 2/1998 | Orgill et al. |
| RE35,748 | E | 3/1998 | Luck et al. |
| 5,759,582 | A | 6/1998 | Leong et al. |
| 5,773,019 | A | 6/1998 | Ashton et al. |
| 5,783,214 | A | 7/1998 | Royer |
| 5,834,232 | A | 11/1998 | Bishop et al. |
| 5,948,427 | A | 9/1999 | Yamamoto et al. |
| 5,981,568 | A | 11/1999 | Kunz et al. |
| 6,124,273 | A | 9/2000 | Drohan et al. |
| 6,179,834 | B1 | 1/2001 | Buysse et al. |
| 6,210,429 | B1 | 4/2001 | Vardi et al. |
| 6,248,110 | B1 | 6/2001 | Reiley et al. |
| 6,287,765 | B1 | 9/2001 | Cubicciotti |
| 6,291,582 | B1 | 9/2001 | Dordick et al. |
| 6,342,250 | B1 | 1/2002 | Masters |
| 6,371,988 | B1 | 4/2002 | Pafford et al. |
| 8,153,591 | B2 | 4/2012 | Masters et al. |
| 2001/0008636 | A1 | 7/2001 | Yamamoto et al. |
| 2001/0020086 | A1 | 9/2001 | Hubbell et al. |
| 2002/0028243 | A1 | 3/2002 | Masters |
| 2002/0052572 | A1 | 5/2002 | Franco et al. |
| 2002/0065553 | A1 | 5/2002 | Weber |
| 2003/0028204 | A1 | 2/2003 | Li et al. |
| 2004/0002558 | A1 | 1/2004 | McKay |
| 2006/0210601 | A1 | 9/2006 | Yunoki et al. |

FOREIGN PATENT DOCUMENTS

| | | |
|---|---|---|
| CA | 1 245 527 | 11/1988 |
| CA | 2171047 | 3/1996 |
| CA | 2134997 | 5/1996 |
| CA | 2192520 | 9/1997 |
| CA | 2175722 | 11/1997 |
| CA | 2185740 | 3/1998 |
| EP | 0 258 780 A2 | 3/1988 |
| EP | 0 567 234 A1 | 10/1993 |
| EP | 0 636 378 A1 | 2/1995 |
| WO | WO 93/24150 | 12/1993 |
| WO | WO 97/32543 | 9/1997 |
| WO | WO 97/32544 | 9/1997 |
| WO | WO 97/41803 | 11/1997 |
| WO | WO 99/32613 | 7/1999 |
| WO | WO 01/83522 A2 | 11/2001 |
| WO | WO 01/87267 A1 | 11/2001 |

OTHER PUBLICATIONS

AAPS: Annual Meeting & Exposition, *Symposia Abstracts & Biographies,* Boston, MA, Nov. 2, 1997, pp. 25-27.

(56) References Cited

OTHER PUBLICATIONS

Abbott et al., *Vascular Grafts: Characteristics and Routine Selection of Prostheses*, Vascular Surgery, a Comprehensive Review, 5$^{th}$ Edition, 1998.
Abstracts, *Eighth International Symposium on Recent Advances in Drug Delivery Systems*, Feb. 24, 1997, Salt Lake City, UT, pp. 36-39, 138-140.
*American Red Cross Open to Partners for New Fibrin Sealant*, Genetic Engineering News, Mar. 1995, p. 30.
Anderson, *Characterization of Silk-like Proteins and Processing for Biomedical Applications*, Protein-Based Materials, 1997, pp. 371-423.
*The Biological Production of Protein Polymers and Their Use*, Trends in Biotechnology, Nov. 1990, vol. 8, No. 11.
Cappello et al., *Microbial Production of Structural Polymers*, (ed. Mobley), 1994 Carl Hanser Verlag, Munich, pp. 35-92.
Cappello et al., *Genetic Engineering of Structural Protein Polymers*, Biotechnology Progress, 1990, pp. 198-202.
Cappello, *Protein Engineering for Biomaterials Applications*, Current Opinion in Structural Biology, 1992, vol. 2, pp. 582-586.
Caruana, *New Drugs Spur Novel Delivery Systems*, Chemical Engineering Progress, Jul. 1997, pp. 15-19.
Choi et al., Implantation Biology: The Host Response and Biomedical Devices. *The Effect of Biomaterials on the Host*, CRC Press, Boca Raton 405 pages, 1994, Chapter 3, pp. 39-53.
Chvapil et al., *Some Chemical and Biological Characteristics of a New Collagen-Polymer\* Compound Material*, J. Biomed Mater. Res., 1969, vol. 3, pp. 315-331.
Davis et al., *Chemically Cross-Linked Albumin Microspheres for the Controlled Release of Incorporated Rose Bengal After Intramuscular Injection Into Rabbits*, Journal of Controlled Release, 4 (1987) 293-302.
Dickinson et al., *Biodegradation of a poly(α-amino acid) hydrogel. I. In vivo*, Journal of Biomedical Materials Research, vol. 15, pp. 577-589 (1981).
Drug Delivery Systems (Program), Feb. 1998, San Francisco.
Dunn et al., *Biomaterials Used in Orthopaedic Surgery*, Implantation Biology, CRC Press, Boca Raton, 1994, pp. 229-252.
Dutton, *Tissue Engineering: Continued Growth Expected as New Techniques Evolve*, Genetic Engineering News, Apr. 1998, pp. 21, 37.
Fernandes et al., *Regulation of Polymeric Implants for Site-specific Drug Delivery*, Polymeric Site-specific Pharmcotherapy, Chapter 16, Jul. 1994, pp. 424-441.
Ghandehari et al., *Genetic Engineering of Protein-Based Polymers: Potential in Controlled Drug Delivery*, Pharmaceutical Research, vol. 15, No. 6, 1998, pp. 813-815.
*Handbook of Food Science, Technology and Engineering*, Yiu, Hu H. (editor), 2006, CRC Press.
Harvey, *Utilizing Prostheses for Drug Delivery*, Implantation Biology, CRC Press, Boca Raton, 1994, pp. 329-345.
Heller et al., *Controlled release of water-soluble macromolecules from Bioerodible Hydrogels*, Biomaterials 1983, vol. 4, October, pp. 262-266.
Kelly, *Researchers Advancing Biopolymer Systems as Vehicles for Delivering Drugs*, Genetic Engineering News, May 15, 1997, pp. 1, 25, 32, 35, 36, 41.
Langer, *1994 Whitaker Lecture: Polymers for Drug Delivery and Tissue Engineering*, Annals of Biomedical Engineering, 1995, vol. 23, pp. 101-111.
Lewis, *New Directions in Research on Blood Substitutes*, Genetic Engineering News, Jun. 15, 1997, pp. 1, 10, 12, 20, 26, 33, 35, 36, 41.
Li et al., *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.
Masters et al., *Liposphere Local Anesthetic Timed-Release for Perineural Site Application*, Pharmaceutical Research, vol. 15, No. 7, 1998, pp. 1038-1045.
Masters et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.
Masters, Course Syllabus for Mayo Graduate Course, *Polymeric Site-Specific Drug Delivery*, Apr. 1998.
Masters et al., *Prolonged Regional Nerve Blockade by Controlled Release of Local Anesthetic from a Biodegradable Polymer Matrix*, Anesthesiology, vol. 79, No. 2, 1993, pp. 340-346.
Masters, *Drug Delivery to Peripheral Nerves*, Polymeric Site-Specific Pharmacotherapy, 1994, pp. 443-455.
Matsui et al, JP 06-125975A, 1994, Machine Translation, obtained Oct. 24, 2011.
Morrione, *The Formation of Collagen Fibers by the Action of Heparin on Soluble Collagen: An Electron Microscope Study*, 1952, J. Exp. Med., 96(2):107-114.
Morrow, *Companies to Take Broad Range of Approaches to Develop Rheumatoid Arthritis Therapies*, Genetic Engineering News, Jan. 15, 1997, pp. 1, 7, 9, 24.
Nomura et al., *Preparation and Some Properties of Type I Collagen from Fish Scales*, 1996, Biosci. Biotech. Biochem., 60(12):2092-2094.
Ohtani, *Three-Dimensional Organization of the Collagen Fibrillar Framework of the Human and Rat Livers*, Arch. Histo. Cytol., vol. 51, No. 5, 1988, pp. 473-788.
Peppas et al., *New Challenges in Biomaterials*, Science, Mar. 1994, vol. 263, pp. 1715-1720.
Polymeric Materials Encyclopedia, Salamone, J.C. (editor), 1996, CRC Press. (see p. 7451).
Pramik, *Drug Delivery Firms Focus on Controlled Release Techniques*, Genetic Engineering News, Oct. 1, 1996, pp. 1, 38, 40.
Pramik, *Positive Clinical Results in Pulmonary Drug Delivery: Inhaled Insulin Effective as Injected Drug*, Genetic Engineering News, Jul. 1998, vol. 18, No. 13, pp. 1, 12, 35, 46.
Protein Polymer Technologies: 1994 Annual Report, *BioEngineered Tissue Repair and Regeneration*.
R&D, A Cahners Publication, *BioDerived Materials*, Jun. 1990, p. 58.
Ranade, *Drug Delivery Systems: 3A. Role of Polymers in Drug Delivery*, J. Clin. Pharmacol., 1990, 30:10-23.
Ranade, *Drug Delivery Systems: 3A. Role of Polymers in Drug Delivery*, J. Clin. Pharmacol., 1990, 30:107-120.
Ratner et al., *An Introduction to Materials in Medicine*, Biomaterials Science, 1996.
Sammi Gelatin, http://sammi-gelain.com/em2.html, 2003, accessed online Jul. 20, 2009.
Sedlak, *Hyal Pharmaceutical Looks for Home Run with HIT Drug Delivery System*, Genetic Engineering News, Sep. 1, 1995, p. 16.
Sedlak, *Signal Transduction Companies Moving Some Products to the Clinical Testing Environment*, Genetic Engineering News, Mar. 15, 1997, vol. 17, No. 6, pp. 1, 27, 36.
Skarda et al., *Biodegradable Hydrogel for Controlled Release of Biologically actve Macromolecules*, Journal of Bioactive and Compatible Polymers, vol. 8, Jan. 1993, pp. 24-40.
*Tissue Engineering*, Genetic Engineering News, Jan. 1998, pp. 33.
Urry et al., *Protein-Based Materials with a Profound Range of Properties and Applications: The Elastin $\Delta T_t$ Hydrophobic Paradigm*, Protein-Based Materials, 1997, pp. 133-177.
http://www.merriam-webster.com/dictionary/binding (accessed Jan. 24, 2009).
International Preliminary Report on Patentability for International Application No. PCT/US2004/027975, dated Nov. 6, 2007, 6 pages.
European Patent Office Communication for Application No. 04 782 454.5-1219, dated Jul. 25, 2012, 7 pages.
Application and File History for U.S. Patent No. 8,153,591, issued Apr. 10, 2012. Inventors: David B. Masters et al.

\* cited by examiner

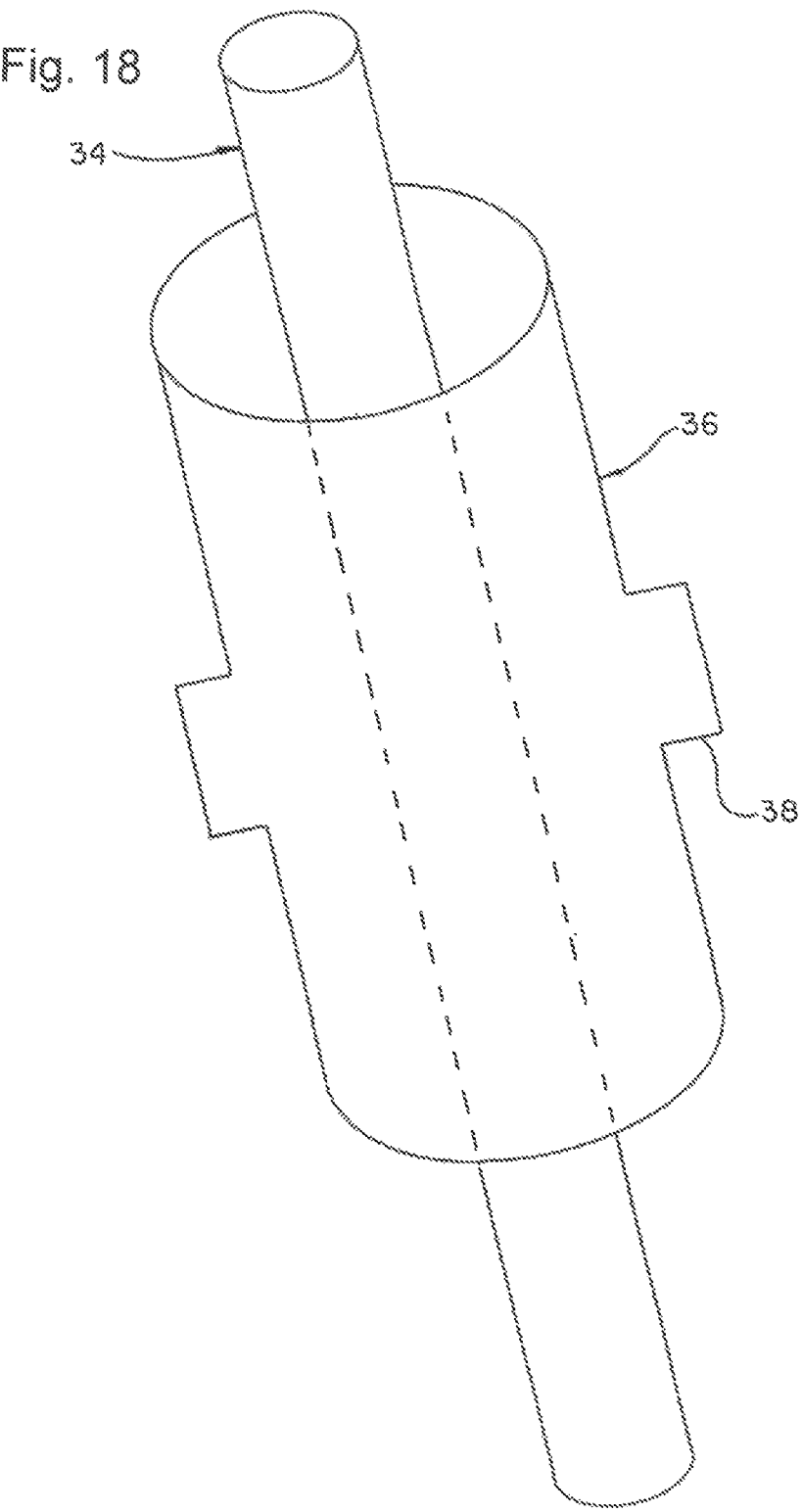

WOUND TREATMENTS WITH CROSSLINKED PROTEIN AMORPHOUS BIOMATERIALS

CROSS-REFERENCE TO RELATED APPLICATION

This application is a continuation application of U.S. application Ser. No. 10/929,117 filed on Aug. 26, 2004, and claims priority to U.S. Provisional Application Ser. No. 60/497,824, filed on Aug. 26, 2003. The contents of these two previously mentioned applications are incorporated by reference herein.

FIELD OF THE INVENTION

The present invention relates to protein biocoacervates and biomaterials and the methods of making and using protein biocoacervates and biomaterials. More specifically the present invention relates to protein biocoacervates and biomaterials that may be utilized for various medical applications including, but not limited to, drug delivery devices for the controlled release of pharmacologically active agents, coated medical devices (e.g. stents, valves . . . ), vessels, tubular grafts, vascular grafts, wound healing devices including protein suture biomaterials and biomeshes, dental plugs and implants, skin/bone/tissue grafts, tissue fillers, protein biomaterial adhesion prevention barriers, cell scaffolding and other biocompatible biocoacervate or biomaterial devices.

BACKGROUND OF THE INVENTION

Protein materials are generally present in the tissues of many biological species. Therefore, the development of medical devices that utilize protein materials, which mimic and/or are biocompatible with the host tissue, have been pursued as desirable devices due to their acceptance and incorporation into such tissue. For example the utilization of protein materials to prepare drug delivery devices, tissue grafts, wound healing and other types of medical devices have been perceived as being valuable products due to their biocompatibility potential.

The use of dried protein, gelatins and/or hydrogels have previously been used as components for the preparation of devices for drug delivery, wound healing, tissue repair, medical device coating and the like. However, many of these previously developed devices do not offer sufficient strength, stability and support when administered to tissue environments that contain high solvent content, such as the tissue environment of the human body. Furthermore, the features of such medical devices that additionally incorporated pharmacologically active agents often provided an ineffective and uncontrollable release of such agents, thereby not providing an optimal device for controlled drug delivery.

A concern and disadvantage of such devices is the rapid dissolving or degradation of the device upon entry into an aqueous or high solvent environment. For example, gelatins and compressed dry proteins tend to rapidly disintegrate and/or lose their form when placed in an aqueous environment. Therefore, many dried or gelatin type devices do not provide optimal drug delivery and/or structural and durability characteristics. Also, gelatins often contain large amounts of water or other liquid that makes the structure fragile, non-rigid and unstable. It is also noted that the proteins of gelatins usually denature during preparation caused by heating, the gelation process and/or crosslinking procedures, thereby reducing or eliminating the beneficial characteristics of the protein. Alternatively, dried protein devices are often very rigid, tend to be brittle and are extremely susceptible to disintegration upon contact with solvents. The deficiencies gelatins and dried matrices have with regards to rapid degradation and structural limitations make such devices less than optimal for the controlled release of pharmacologically active agents, or for operating as the structural scaffolding for devices such as vessels, stents or wound healing implants.

Hydrogel-forming polymeric materials, in particular, have been found to be useful in the formulation of medical devices, such as drug delivery devices. See, e.g., Lee, *J. Controlled Release*, 2, 277 (1985). Hydrogel-forming polymers are polymers that are capable of absorbing a substantial amount of water to form elastic or inelastic gels. Many non-toxic hydrogel-forming polymers are known and are easy to formulate. Furthermore, medical devices incorporating hydrogel-forming polymers offer the flexibility of being capable to be implantable in liquid or gelled form. Once implanted, the hydrogel forming polymer absorbs water and swells. The release of a pharmacologically active agent incorporated into the device takes place through this gelled matrix via a diffusion mechanism.

However, many hydrogels, although biocompatible, are not biodegradable or are not capable of being remodeled and incorporated into the host tissue. Furthermore, most medical devices comprising of hydrogels require the use of undesirable organic solvents for their manufacture. Residual amounts of such solvents could potentially remain in the medical device, where they could cause solvent-induced toxicity in surrounding tissues or cause structural or pharmacological degradation to the pharmacologically active agents incorporated within the medical device. Finally, implanted medical devices that incorporate pharmacologically active agents in general, and such implanted medical devices comprising hydrogel-forming polymers in particular, oftentimes provide suboptimal release characteristics of the drug(s) incorporated therein. That is, typically, the release of pharmacologically active agents from an implanted medical device that includes pharmacologically active agent(s) is irregular, e.g., there is an initial burst period when the drug is released primarily from the surface of the device, followed by a second period during which little or no drug is released, and a third period during which most of the remainder of the drug is released or alternatively, the drug is released in one large burst.

Also, particles made from decellularized tissue, such as human, bovine or porcine tissue, have also been utilized in various medical applications. These decellularized tissue particles have been utilized in various applications as subcutaneous tissue fill materials. Furthermore, these substances have been shown to have some biocompatible properties, but generally are difficult to work with due to the already established matrix present in such materials. Furthermore, such tissue related materials are not conducive to the homogenous distribution of pharmacologically active agents within their matrix structure.

Additionally, other polymeric materials, such as polyvinyl pyrrolidone, polyvinyl alcohols, polyurethanes, polytetrafluoroethylene (PTFE), polypolyvinyl ethers, polyvinylidene halides, polyacrylonitrile, polyvinyl ketones; polyvinyl aromatics, ethylene-methyl methacrylate copolymers, polyamides, polycarbonates, polyoxymethylenes, polyimides, polyethers and other polymeric materials have been utilized as coatings for medical devices, drug delivery devices, tissue fillers or grafts, sutures and for other medical applications. These materials possess some biocompatible attributes, but are limited by their capacity to be non-thrombogenic, to be non-inflammatory, to allow direct cell integration, to deliver therapeutic agents, to allow regeneration of host tissue into the graft and/or to allow other graft materials to adhere to their surface.

SUMMARY OF THE INVENTION

The present invention relates to protein biocoacervates and related biomaterials and the methods of making and using protein biocoacervates and the related biomaterials. More specifically the present invention relates to protein biocoacervates and related biomaterials that may be utilized for various medical applications including, but not limited to, drug delivery devices for the controlled release of pharmacologically active agents, coated stent devices, vessels, tubular grafts, vascular grafts, wound healing devices including protein suture biomaterials and biomeshes, skin/bone/tissue grafts, tissue fillers (e.g. cosmetic wrinkle fillers), protein biomaterial adhesion prevention barriers, cell scaffolding and other biocompatible biocoacervate or biomaterial devices.

Generally, the protein biocoacervates, related biomaterials and devices derived from these biocoacervates or related biomaterials is an amorphous material comprising one or more biocompatible primary proteins, one or more glycosaminoglycans and one or more biocompatible solvents. It is noted that the term glycosaminoglycan may also be considered to include mucopolysaccharides and proteoglycans. Additionally, the biocoacervates, biomaterials or their corresponding devices may also include one or more secondary proteins, one or more pharmacologically active agents and/or one or more additive materials to provide a therapeutic entity or enhance the chemical and/or mechanical properties of the biocoacervate or biomaterial.

The present invention also relates to a method of making a protein biocoacervate and/or biomaterial and corresponding devices. The method of preparation includes first forming a biocompatible coacervate including one or more biocompatible primary proteins, one or more glycosaminoglycans and one or more biocompatible solvents. In various embodiments, the biocoacervate is formed by also including one or more secondary proteins. The biocoacervate is generally assembled by combining one or more primary proteins such as collagen, fibrin or fibronectin and one or more glycosaminoglycans such as heparin, chondroiten sulfate or heparin sulfate to a heated and optionally stirred solution of one or more biocompatible solvents such as water, DMSO, or ethanol. One or more secondary proteins such as elastin or albumen may also be added to the primary protein/glycosaminoglycan solution. Upon adding the glycosaminoglycan to the heated solution containing the primary protein(s), and in various embodiments the secondary protein, an amorphous body falls out. The amorphous protein body generally falls out of the solution as an amorphous precipitate material allowing it to be easily extracted from the solution. Generally, the precipitant of the present invention falls out of solution due to a chemical and/or physical change thereby forming the water insoluble amorphous biocoacervate. Once extracted from the solution, the amorphous material is allowed to cool thereby forming a cohesive elastic coacervate. It is noted that the material has elastic mechanical properties similar to the material utilized in rubberbands and is capable of being melted and formed into any type shape or configuration. The biocoacervate is generally stable in water. However, the biocoacervate dissolves when placed in saline solution. A biomaterial that does not dissolve in saline solution may be produced from the biocoacervate by setting the biocoacervate utilizing a crosslinking agent, such as gluteraldehyde, utilizing a crosslinking technique like dehydrothermal processes, such as heat radiation, and/or by utilizing any crosslinking means that cause the proteins and/or glycosaminoglycans to crosslink.

As previously mentioned, the biocoacervate or biomaterial may also optionally include additional polymeric materials and/or therapeutic entities, such as one or more pharmacologically active agents, that would provide additional beneficial characteristics or features to the coacervate. Generally, these materials and/or entities may be added to the solution during the formation of the coacervate. Alternatively, these materials and/or entities may be added after the coacervate has been formed utilizing any means to disperse the agent(s) within the biocoacervate such as dissolving the agent(s) into the melted form of the coacervate or allowing diffusion and/or loading the agent(s) into the unmelted coacervate.

The above described process has many advantages if one or more pharmacologically active agents are incorporated into the biocoacervate. For example, the controlled release characteristics of the biocoacervates and biomaterials of the present invention provide for a higher amount of pharmacologically active agent(s) that may be incorporated into the biocoacervate or biomaterial. Additionally, the pharmacologically active agent(s) may be substantially homogeneously distributed throughout biocoacervate, biomaterial or corresponding devices. This homogenous distribution provides for a more systematic and consistent release of the pharmacologically active agent(s). As a result, the release characteristics of the pharmacologically active agent from the biocoacervate, biomaterial and/or device are enhanced.

Inasmuch as the biocoacervates, biomaterials and corresponding devices of the present invention provide the sustained release of one or more pharmacologically active agents in a rate controllable fashion, they are also capable of delivering other migration-vulnerable and/or reactive drug delivery devices and furthermore are produced in a manner that reduces, if not eliminates, the risk of residual solvent toxicity or adverse tissue reaction. Also, the biocoacervates, biomaterials and corresponding devices of the present invention provide a method of effecting a local therapeutic response in a patient in need of such treatment. Specifically, the method of using the biocoacervate, biomaterial or related devices of the present invention comprises the step of administering the biocoacervate, biomaterial or corresponding device to the site at which a local therapeutic response is desired. Additionally, the biocoacervates, biomaterials and corresponding devices may be administered for systemic delivery of pharmacologically active agents, including oral, as well as nasal, mucosal, intraocular pulmonary, subcutaneous, intradermal, intrathecal, sublingual, epidural, subdural, tissue implantable or any other parenteral mode of delivery. Preferably, the therapeutic response effected is an analgesic response, an anti-inflammatory response, an anesthetic response, a response preventative of an immunogenic response, an anti-coagulatory response, a genetic response, an antimitotic response, a protein assembly response, an antibacterial response, a vaccination response, combinations of these, and the like. As used herein, unless stated otherwise, all percentages are percentages based upon the total mass of the composition being described, e.g., 100% is total.

The foregoing and additional advantages and characterizing features of the present invention will become increasingly apparent to those of ordinary skill in the art by references to the following detailed description and to the drawings.

BRIEF DESCRIPTION OF THE FIGURES

The above mentioned and other advantages of the present invention, and the manner of attaining them, will become more apparent and the invention itself will be better understood by reference to the following description of the embodiments of the invention taken in conjunction with the accompanying drawing, wherein:

FIG. 18 depicts an embodiment of a protrusion device 34 that includes a port seal.

DETAILED DESCRIPTION OF THE INVENTION

The embodiments of the invention described below are not intended to be exhaustive or to limit the invention to the precise forms disclosed in the following detailed description. Rather, the embodiments are chosen and described so that others skilled in the art may appreciate and understand the principles and practices of the present invention.

The biocoacervates, biomaterials and devices of the present invention comprise an amorphous material that generally includes one or more primary proteins, one or more glycosaminoglycans and one or more biocompatible solvents. The amorphous material of the present invention tends to have no real or apparent crystalline or fibrous form that can be seen by the naked eye or by light microscope at 400× or less. Such materials are different from other protein and glycosaminoglycan materials, which tend to be crystalline, fibrous or appears similar to balls of yarn. Also the biocoacervate and a number of the biomaterial embodiments of the present invention tend to have thermoplastic and viscoelastic properties. In various embodiments of the present invention the biocoacervates, biomaterials and devices may also include one or more secondary proteins.

Figure 1:
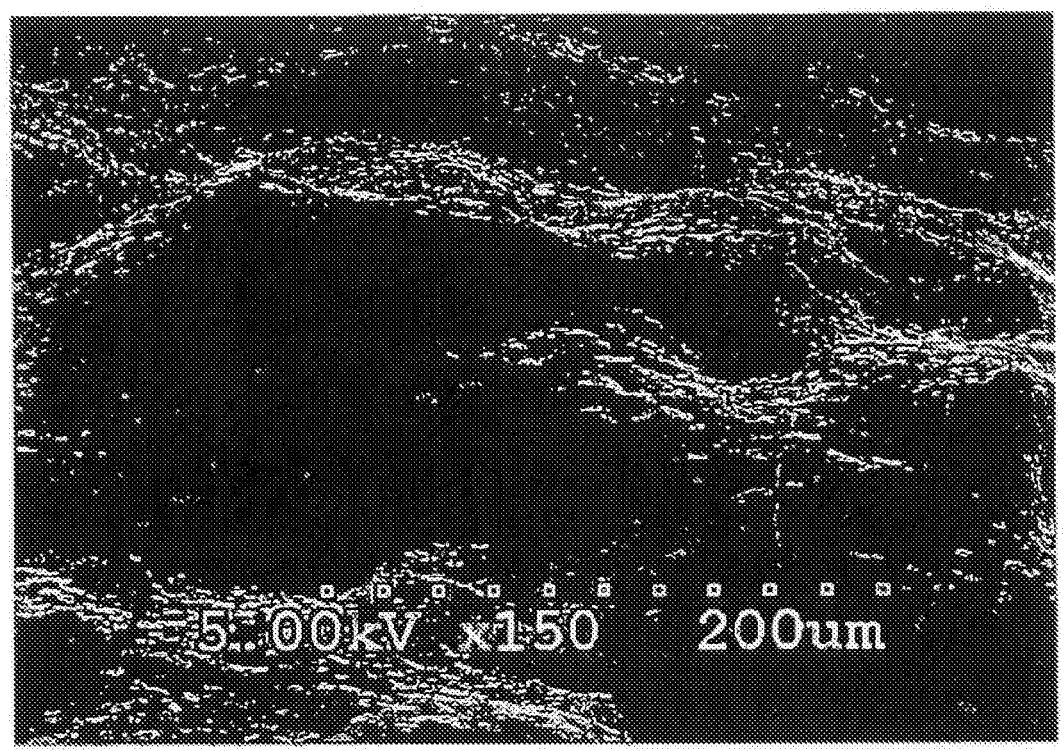
FIG. 1 depicts a magnified view of an embodiment of the biomaterial of the present invention illustrating the aggregated proteoids.
Figure 2A:
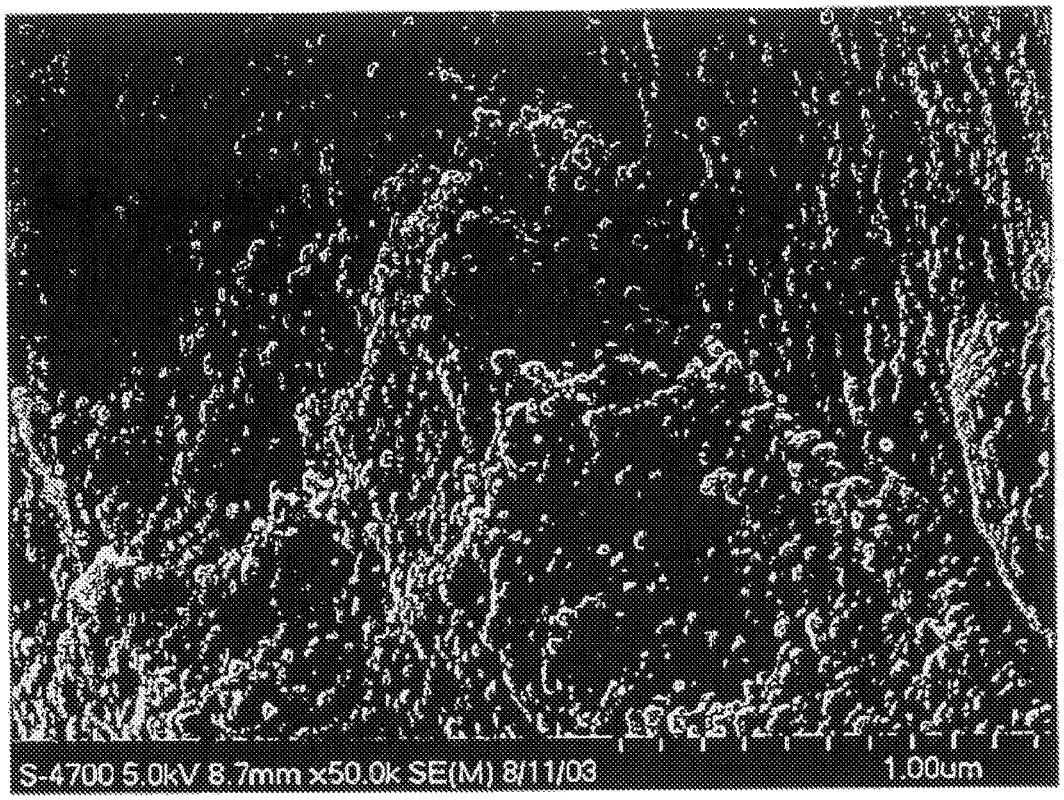
FIG. 2A-C depicts a magnified view of an embodiment of the biomaterial of the present invention illustrating the aggregated proteoids.
Figure 2B:
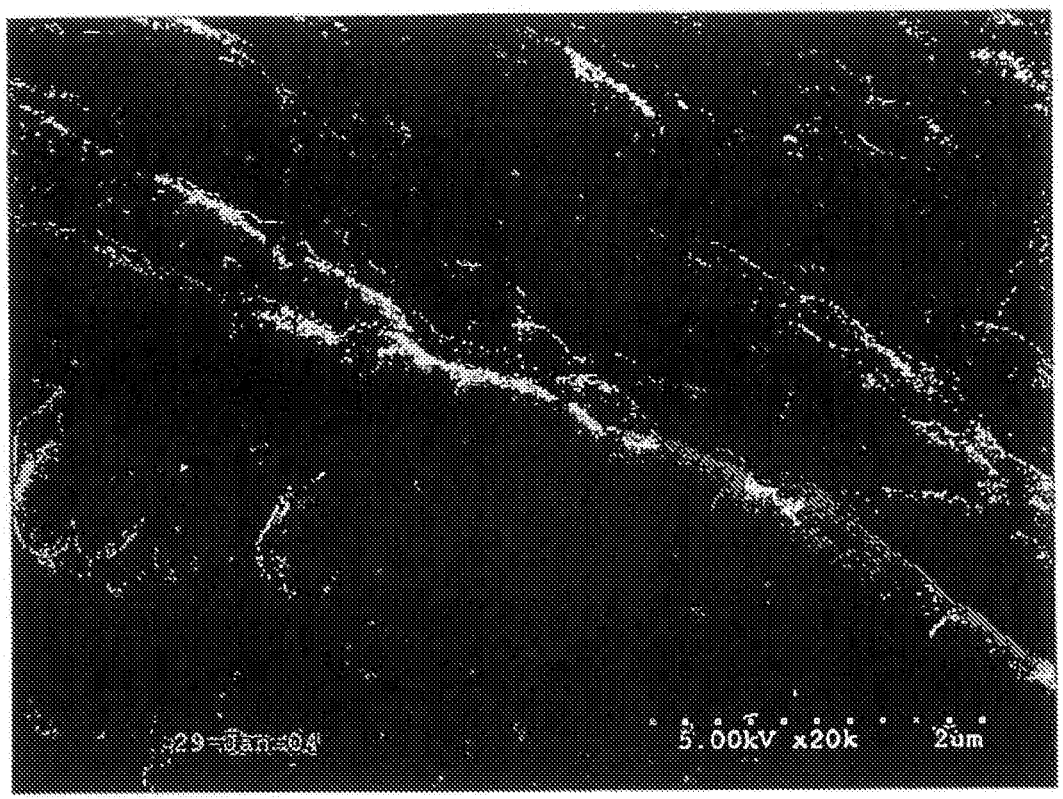
Figure 2C:
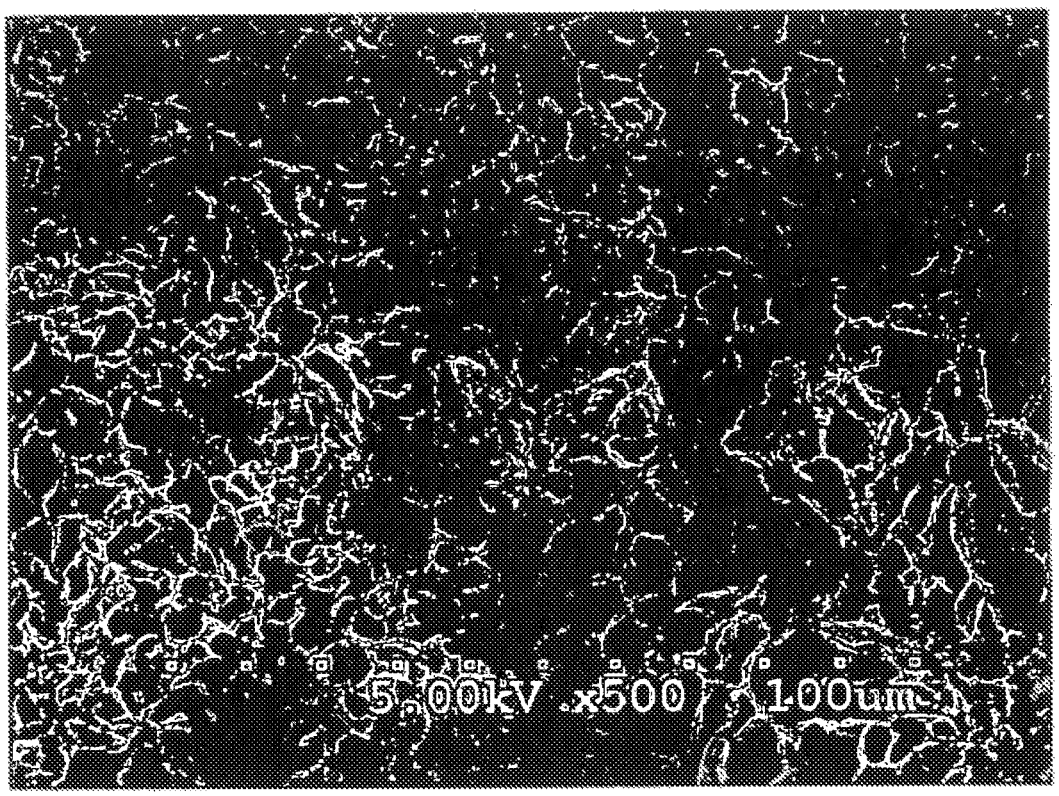

FIGS. 1 and 2A-B depict a magnified view of embodiments of the biomaterials of the present invention. As depicted in these figures, various embodiments of the biocoacervate of the present invention include a plurality of individual spherical complexes (hereinafter referred to as "proteoids"), which interact with each other to form the biocoacervate. Generally, the proteoids found in the present invention are small microspheres comprising at least a primary protein, a glycosaminoglycan and a biocompatible solvent. The proteoids will tend to aggregate together to form the amorphous biocoacervate embodiments of the present invention. Also, it has been found that under certain conditions the proteoids can undergo strong intermolecular bonding that may alter their shape. FIG. 2C depicts an embodiment of the biocoacervate that has been crosslinked and freeze fractured to illustrate that the proteoids of this embodiment include inner cavities and crosslinks that hold the proteoids together into a single mass. These proteoids or spherical complexes generally range from 0.001 to 100 microns in size, in various embodiments 0.1 to 10 microns, but may vary in size depending upon the amount of swelling they experience. The swelling of biocoacervates including the proteoids may be controlled by crosslinking, pH, compression, salt content, solvent content (e.g. water or alcohol content) and/or temperature. Furthermore, the amount of swelling may be controlled by adjusting the various degrees of crosslinking of the biocoacervate before exposing the material to one or more solutions.

Additionally, embodiments of the biocoacervates, biomaterials and devices of the present invention may also include one or more therapeutic pharmacologically active agents and/or one or more additive materials, such as structural or polymeric materials. It is noted that additional additive materials, such as humectants, biocompatible polymers (e.g. proteins, polyanhydride, polylactic acid, polyurethane and the like) and/or therapeutic entities, such as stents and other medical devices may be included in the material to provide various beneficial features such as mucoadhesion, strength, elasticity, structure, enhanced biocompatibility, enhanced drug delivery and drug absorption, therapeutic functions or any other desirable characteristics. In various embodiments of the present invention, the biocoacervates or biomaterials possess a relatively homogeneous distribution of the components, including a homogenous distribution of any pharmacologically active agents and additive materials.

The biocoacervates, biomaterials and the related devices of the present invention are designed to retain the protein's natural activity and possess the capability of being formed into various sizes and configurations with structural integrity. Embodiments of the biocoacervates, biomaterials and the related devices are further designed to mimic the architectural framework of the body to support natural tissue growth. In various embodiments of the present invention the biocoacervates, biomaterials and the related devices of the present invention are biointegratable thereby allowing the integration and remodeling of the material by the host tissue.

As previously mentioned, the biocoacervates, biomaterials and the related devices normally comprise one or more biocompatible primary proteins and, in various embodiments, one or more secondary proteins. The primary and secondary proteins are generally soluble or are solubilized. Primary proteins normally have an affinity to bind with glycosaminoglycans and in some instances other proteins thereby indicating that functional groups are present on the primary proteins that attract and retain the glycosaminoglycans and possibly other proteins. Additionally, primary proteins when mixed with glycosaminoglycans in solution under proper conditions will generally form a precipitate that falls out of solution, whereas the secondary proteins will not form such a precipitate when placed in solution with glycosaminoglycans. Additionally, secondary proteins generally have a more limited binding affinity with glycosaminoglycans than their primary protein counterparts, but are attracted and retained by the primary proteins in the presence of glycosaminoglycans. However, secondary proteins have been found to add very beneficial characteristics to the biocoacervates of the present invention, such as elasticity, strength, biodurability, biocompatibility and the like. Generally, the amount of primary protein found in embodiments of the biocoacervate or biomaterials of the present invention may vary between from about 10% to about 90%, preferably from about 20% to 80% by weight, and most preferably from about 50% to 70% by weight based upon the weight of the final biocoacervate or biomaterial. Alternatively, the amount of secondary protein may vary between from about 0% to about 40%, preferably from about 10% to 30% by weight, and most preferably from about 15% to 25% by weight based upon the weight of the final biocoacervate or biomaterial.

The primary and secondary proteins utilized in the present invention may be synthetic proteins, genetically-engineered proteins, natural proteins or any combination thereof. In many embodiments of the present invention, the biocoacervates, biomaterials and the related devices include water-absorbing, biocompatible primary and secondary proteins. The utilization of a water-absorbing biocompatible protein included in the biocoacervate or biomaterial provides the advantage that, not only will the biocoacervates or biomaterials be bioresorbable, but may remodel to mimic and support the tissue it contacts. That is, the metabolites of any degradation and/or resorption of the water-absorbing biocompatible protein may be reused by the patient's body rather than excreted.

Additionally, the primary and secondary proteins of the present invention are generally purified and in a free-form state. Normally, free-form proteins are comprised of protein molecules that are not substantially crosslinked to other protein molecules, unlike tissues (e.g. decellularized tissue) or gelatins. Normally, tissue or gelatin is already in a crosslinked matrix form and is thereby limited in forming new intermolecular or intramolecular bonds. Therefore, the free-form protein molecules when added to solvent have the capacity to freely associate or intermingle with each other and other molecules or particles, such as solvents, pharmacologically active agents, additives and other proteins to form a homogeneous structure. Additionally, the binding sites of the free-form primary proteins for the attraction and retention of glycosaminoglycans or secondary proteins are generally available for binding whereas proteins derived from tissues and gelatins have generally lost some or most of its binding or interaction capability.

As previously suggested, the primary and secondary proteins utilized may either be naturally occurring, synthetic or genetically engineered. Naturally occurring primary proteins that may be utilized in biocoacervates, biomaterials and related devices of the present invention include, but are not limited to the following and their derivatives: collagen, bone morphogenic protein and its isoforms that contain glucosaminoglycan binding sites, albumin, interleukins, epidermal growth factors, fibronectin, laminin, thrombin, aprotinin, antithrombin III and any other biocompatible natural protein that includes glucosaminoglycan binding sites. Naturally occurring secondary proteins that may be utilized in biocoacervates, biomaterials and related devices of the present invention include, but are not limited to the following and their derivatives: fibrin, fibrinogen, elastin, albumin, ovalbumin, keratin, silk, silk fibroin, actin, myosin, thrombin, aprotinin, antithrombin III and any other biocompatible natural protein that have an affinity to primary proteins in the presence of glucosaminoglycans. Examples of primary and secondary proteins that are commercially available and may be utilized in some embodiments of the present invention include Type I soluble or insoluble collagen, insoluble or soluble elastin, and soluble albumen manufactured by Kensey Nash Corporation, 55 East Uwchlan Avenue, Exton, Pa. 19341, Sigma-Aldrich Corporation, St. Louis, Mo., USA or Elastin Products Company, Inc., P.O. Box 568, Owensville, Mo., USA 65066. It is noted that in various embodiments of the present invention, the insoluble proteins listed above would be processed to a soluble form prior to or during synthesis of a biocoacervate or biomaterial. It is further noted that combinations of natural proteins may be utilized to optimize desirable characteristics of the resulting biocoacervates and biomaterials, such as strength, degradability, resorption, etc. Inasmuch as heterogeneity in molecular weight, sequence and stereochemistry can influence the function of a protein in a biocoacervate or biomaterial, in some embodiments of the present invention synthetic or genetically engineered proteins are preferred in that a higher degree of control can be exercised over these parameters.

As previously suggested the primary and secondary proteins of the present invention are generally purified proteins. The purity of each natural protein component mixed in the solution phase (the process of making the coacervates and biomaterials will be described further below) during production of the coacervate include 20% or less other proteins or impurities, preferably 10% or less other proteins or impurities, more preferably 3% or less other proteins or impurities and if available ideally 1% or less other proteins or impurities.

Synthetic primary and secondary proteins are generally prepared by chemical synthesis utilizing techniques known in the art and generally mimic the equivalent natural protein's or natural protein derivative's chemical and/or structural makeup. Furthermore, individual proteins may be chemically combined with one or more other proteins of the same or different type to produce a dimer, trimer or other multimer. A simple advantage of having a larger protein molecule is that it will make interconnections with other protein molecules to create a stronger coacervate or biomaterial that is less susceptible to dissolving in aqueous solutions and provides additional protein structural and biochemical characteristics.

Additionally, protein molecules can also be chemically combined to any other chemical so that the chemical does not release from the biocoacervate or biomaterial. In this way, the chemical entity can provide surface modifications to the biocoacervate or biomaterial or structural contributions to the biocoacervate or biomaterial to produce specific characteristics. The surface modifications can enhance and/or facilitate cell attachment depending on the chemical substance or the cell type. The structural modifications can be used to facilitate or impede dissolution or enzymatic degradation of the biocoacervate or biomaterial, as well as increase the affinity of the biocoacervate to interact (e.g. bind or coat) with other materials.

Synthetic biocompatible proteins may be cross-linked, linked, bonded, chemically and/or physically linked to pharmacological active agents, enzymatically, chemically or thermally cleaved and utilized alone or in combination with other biocompatible proteins or partial proteins e.g. peptides, to form the biocoacervates or biomaterials. Examples of such synthetic biocompatible proteins include, but are not limited to heparin-protein, heparin-polymer, chondroitin-protein, chondroitin-polymer, heparin-cellulose, heparin-alginate, heparin-polylactide, GAGs-collagen, heparin-collagen, collagen-elastin-heparin, collagen-albumin, collagen-albumin-heparin, collagen-albumin-elastin-heparin, collagen-hyaluronic acid, collagen-chondroitin-heparin, collagen-chondroitin and the like.

A specific example of a particularly preferred genetically engineered primary protein for use in the biocoacervates or biomaterials of the present invention is human collagen produced by FibroGen, Inc., 225 Gateway Blvd., South San Francisco, Calif. 94080. Other examples of particularly preferred genetically engineered proteins for use in the biocoacervates or biomaterials of the present invention are commercially available under the nomenclature "ELP", "SLP", "CLP", "SLPL", "SLPF" and "SELP" from Protein Polymer Technologies, Inc. San Diego, Calif. ELP's, SLP's, CLP's, SLPL's, SLPF's and SELP's are families of genetically engineered protein polymers consisting of silklike blocks, elastin-like blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table A depicts examples of genetically engineered blocks. Table A and a further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

TABLE A

Protein polymer sequences

| Polymer Name | Monomer Amino Acid Sequence |
|---|---|
| SLP 3 | [(GAGAGS)$_9$GAAGY)] |
| SLP 4 | (GAGAGS)$_n$ |
| SLP F | [(GAGAGS)$_9$GAA VTGRGDSPAS AAGY]$_n$ |
| SLP L3.0 | [(GAGAGS)$_9$GAA PGASIKVAVSAGPS AGY]$_n$ |

TABLE A-continued

Protein polymer sequences

| Polymer Name | Monomer Amino Acid Sequence |
|---|---|
| SLP L3.1 | [(GAGAGS)$_9$GAA PGASIKVAVSGPS AGY]$_n$ |
| SLP F9 | [(GAGAGS)$_9$RYVVLPRPVCFEK AAGY]$_n$ |
| ELP I | [(VPGVG)$_4$]$_n$ |
| SELP 0 | [(GVGVP)$_8$(GAGAGS)$_2$]$_n$ |
| SELP 1 | [GAA(VPGVG)$_4$VAAGY(GAGAGS)$_9$]$_n$ |
| SELP 2 | [(GAGAGS)$_6$GAAGY(GAGAGS)$_5$(GVGVP)$_8$]$_n$ |
| SELP 3 | [(GVGVP)$_8$(GAGAGS)$_8$]$_n$ |
| SELP 4 | [(GVGVP)$_{12}$(GAGAGS)$_8$]$_n$ |
| SELP 5 | [(GVGVP)$_{16}$(GAGAGS)$_8$]$_n$ |
| SELP 6 | [(GVGVP)$_{32}$(GAGAGS)$_8$]$_n$ |
| SELP 7 | [(GVGVP)$_8$(GAGAGS)$_6$]$_n$ |
| SELP 8 | [(GVGVP)$_8$(GAGAGS)$_4$]$_n$ |
| KLP 1.2 | [(AKLKLAEAKLELAE)$_4$]$_n$ |
| CLP 1 | [GAP(GPP)$_4$]$_n$ |
| CLP 2 | {[GAP(GPP)$_4$]$_2$GPAGPVGSP}$_n$ |
| CLP-CB | {[GAP(GPP)$_4$]$_2$(GLPGPKGDRGDAGPKGADGSPGPA) GPAGPVGSP}$_n$ |
| CLP 3 | (GAPGAPGSQGAPGLQ)$_n$ |

Repetitive amino acid sequences of selected protein polymers.
SLP = silk like protein;
SLPF = SLP containing the RGD sequence from fibronectin;
SLPL 3/0 and SLPL 3/1 = SLP containing two difference sequences from laminin protein;
ELP = elastin like protein;
SELP = silk elastin like protein;
CLP = collagen like protein;
CLP-CB = CLP containing a cell binding domain from human collagen;
KLP = keratin like protein The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The biocoacervates and biomaterials utilized in various embodiments of the present invention also include one or more glycosaminoglycans, proteoglycans or mucopolysaccharides. Glycosaminoglcans can be derived or synthesized from any source, including artificial, animal or plant sources. Examples of glycosaminoglycans that are utilized in the coacervates and biomaterials of the present invention include but are not limited to the heparin, heparin sulfate, keratan sulfate, dermatin, dermatin sulfate, heparin-hyaluronic acid, chondroitin, chondroitin sulfate (e.g. chondroitin 6-sulfate and chondroitin 4-sulfate), chitin, chitosan, acetyl-glucosamine, hyaluronic acid, aggrecan, decorin, biglycan, fibromodulin, lumican, combinations, glycosaminoglycan complexes or compounds and the like.

The biocoacervates and biomaterials utilized in various embodiments of the present invention also include one or more biocompatible solvents. Any biocompatible solvent may be utilized in the method and corresponding coacervate or biomaterial of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; dimethyl sulfoxide (DMSO); biocompatible alcohols, such as polyols, glycerol, methanol and ethanol; various acids, such as acetic acid, citric acid, ascorbic acid and formic acid; oils, such as olive oil, peanut oil and the like; glycols, such as ethylene glycol; and combinations of these and the like. Preferably, the biocompatible solvent comprises water. The amount of biocompatible solvent utilized in the formation of the present invention will preferably be that amount sufficient to result in the primary and secondary proteins being fluid and flowable enough to allow the protein to enter into solution. Generally, the amount of biocompatible solvent suitable for use in the method of the present invention will range from about 100% to about 50,000% by weight, in some embodiments from about 200% to about 10,000% by weight, and in other embodiments from about 300% to about 2000% by weight, based upon the weight and/or amount of the protein utilized.

In addition to the biocompatible protein(s) and the biocompatible solvent(s), the coacervates or biomaterial that may be utilized in various embodiments of the present invention may include one or more pharmacologically active agents. Generally, the distribution of the pharmacologically active agent is rendered substantially homogenous throughout the resulting coacervate or biomaterial. As used herein, "pharmacologically active agent" generally refers to a pharmacologically active agent having a direct or indirect beneficial therapeutic effect upon introduction into a host. Pharmacologically active agents further includes neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the coacervates, biomaterials and related devices of the present invention include, but are not limited to, (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarryrthmics such as amiodarone, flecamide, disopyramide, procainamide, mexiletene and quinidine;

Antiangina agents such as glyceryl trinitrate, erythrityl tetranitrate, pentaerythritol tetranitrate, mannitol hexanitrate, perhexylene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antiproliferative agents such as paclitaxel, actinomycin D, sirolimus, tacrolimus, everolimus, estradiol and dexamethasone;

Antimigraine preparations such as ergotanmine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Immunosuppressants, antiproliferatives and cytostatic agents such as rapomycin (sirolimus) and its analogs (everolimus and tacrolimus);

Neurotoxins such as capsaicin, botulinum toxin (botox);

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl)indole;

Anti-alzheimer's agents such as tacrine;

Anti-Parkinson's agents such as amantadine, benserazide, carbidopa, levodopa, benztropine, biperiden, benzhexyl, procyclidine and dopamine-2 agonists such as S(−)-2-(N-propyl-N-2-thienylethylamino)-5-hydroxytetralin (N-0923);

Anticonvulsants such as phenyloin, valproic acid, primidone, phenobarbitone, methylphenobarbitone and carbamazepine, ethosuximide, methsuximide, phensuximide, sulthiame and clonazepam;

Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and bromopride;

Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-(α-methyl-19-noriestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Complex carbohydrates such as glucans;

Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Amnioglycoides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in *International Journal of Pharmaceutics*, 111, 223-233 (1994)), methotrexate, procarbazine, 6-mercaptopurine and mucophenolic acid;

Anorectic and weight reducing agents including dexfenfluramine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as benzocaine, bupivacaine, amethocaine, lignocaine, lidocaine, cocaine, cinchocaine, dibucaine, mepivacaine, prilocalne, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.*, 106(5), 1096, (1996)];

Neuromuscular blocking agents such as suxamethonium, alcuronium, pancuronium, atracurium, curarie, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12, B12α, and E, vitamin E acetate and vitamin E sorbate;

Allergens for desensitisation such as house, dust or mite allergens;

Nutritional agents and neutraceuticals, such as vitamins, essential amino acids and fats;

Macromolecular pharmacologically active agents such as proteins, enzymes, peptides, polysaccharides (such as cellulose, amylose, dextran, chitin), nucleic acids, cells, tissues, and the like;

Bone and/or tissue mending biochemicals such as calcium carbonate, calcium phosphate, hydroxyapetite or bone morphogenic protein (BMP);

Angiogenic growth factors such as Vascular Endothelial Growth Factor (VEGF) and epidermal growth factor (EFG), cytokines interleukins, fibroblasts and cytotaxic chemicals; and Keratolytics such as the alpha-hydroxy acids, glycolic acid and salicylic acid; and DNA, RNA or other oligonucleotides.

Additionally, the coacervates and biomaterials of the present invention are particularly advantageous for the encapsulation, incorporation and/or scaffolding of macromolecular pharmacologically active agents such as pharmacologically active proteins, enzymes, peptides, polysaccharides, nucleic acids, cells, tissues, and the like. It is noted that the encapsulation of certain pharmacologically active agents with the biocoacervate or biomaterial of the present invention reduces, if not prevents, the potential for undesirable reaction with bodily fluids or tissues that may otherwise occur upon implantation of a reactive drug delivery device without protective encapsulation. Immobilization of macromolecular pharmacologically active agents into or onto biomaterials can be difficult due to the ease with which some of these macromolecular agents denature when exposed to organic solvents, some constituents present in bodily fluids or to temperatures appreciably higher than room temperature. However, since the method of the present invention utilizes biocompatible solvents such as water, DMSO or ethanol the risk of the denaturation of these types of materials is reduced. Furthermore, due to the size of these macromolecular pharmacologically active agents, these agents may be encapsulated within the coacervates or biomaterials of the present invention and thereby are protected from constituents of bodily fluids that would otherwise denature them. Thus, the coacervates and biomaterials of the present invention allow these macromolecular agents to exert their therapeutic effects, while yet protecting them from denaturation or other structural degradation. Also, embodiments of the present invention include coacervates or biomaterials that provide presentation of therapeutic moieties of attached compounds to the biological surroundings.

Examples of cells which can be utilized as the pharmacologically active agent in the coacervates, biomaterials and related devices of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, endothelial cells, epithelial cells, hepatocytes, T-cells, combinations of these, and the like. As can be seen from this partial list, cells of all types, including dermal, neural, blood, organ, stem, muscle, glandular, reproductive and immune system cells, as well as cells of all species of origin, can be encapsulated and/or attached successfully by this method.

Examples of pharmacologically active proteins which can be incorporated into the coacervates or biomaterials of the present invention include, but are not limited to, hemoglobin, bone morphogenic protein, desmopressin, vasporessin, oxytocin, adrenocorticocotrophic hormone, epidermal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin; oligonucleotides; bacteria and other microbial microorganisms including viruses; monoclonal antibodies, such as herceptin and rituximab; vitamins; cofactors; growth factors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as PHYSICIANS'DESK REFERENCE®: PDR—52 Ed (1998)—MEDICAL ECONOMICS 1974. In consideration of these parameters, it has been found that a wide range exists in the amount of the pharmacologically active agent(s) capable of being incorporated into and subsequently released from or alternatively allowed to exert the agent's therapeutic effects from within the coacervates or biomaterials. More specifically, the amount of pharmacologically active agent that may be incorporated into and then either released from or active from within the coacervates or biomaterials may range from about 0.001% to about 60%, more preferably, from about 0.05% to about 40%, most preferably from about 0.1% to 20%, based on the weight of the coacervate material or biomaterial. It is important to note that the pharmacologically active agents are generally homogenously distributed throughout the coacervate material or biomaterial thereby allowing for a controlled release of these agents.

Finally, one or more additive materials may be added to the coacervate or biomaterial to manipulate the material properties and thereby add additional structure, enhance absorbance of the pharmacologically active agents, enhance membrane permeation by pharmacologically active agents (cell and tissue), enhance mucoadhesion or modify the release of pharmacologically active agents. That is, while a coacervate material or biomaterial that includes a relatively fast-degrading protein material without a particular additive material may readily degrade thereby releasing drug relatively quickly upon insertion or implantation, a coacervate material or biomaterial that includes a particular polymeric material, such as polyanhydride, will degrade slowly, as well as release the pharmacologically active agent(s) over a longer period of time. Examples of biodegradable and/or biocompatible additive materials suitable for use in the coacervate or biomaterial of the present invention include, but are not limited to polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyacetal, poly(lactic acid), poly(ethylene oxide)/poly(butylene terephthalate) copolymer, polycarbonate, poly(tetrafluoroethylene) (PTFE), polycaprolactone, polyethylene oxide, polyethylene glycol, poly(vinyl chloride), polylactic acid, polyglycolic acid, polypropylene oxide, poly(alkylene)glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly (amido amines), fibrin, glycosaminoglycans such as hyaluronic acid or chondroitin sulfate, bioceramic materials such as hydroxyapetite, graphite, flexible fluoropolymer, isobutyl-based, isopropyl styrene, vinyl pyrrolidone, cellulose acetate dibutyrate, silicone rubber, copolymers of these, and the like.

Additionally, hydrophobic additives such as lipids can be incorporated into the coacervates or biomaterials to extend the duration of drug release or facilitate the incorporation of hydrophobic drugs. Exemplary hydrophobic substances include lipids, e.g., tristearin, ethyl stearate, phosphotidycholine, polyethylene glycol (PEG); fatty acids, e.g., sebacic acid erucic acid; combinations of these and the like. A particularly preferred hydrophobic additive useful to extend the release of the pharmacologically active agents comprises a combination of a dimer of erucic acid and sebacic acid, wherein the ratio of the dimer of erucic acid to sebacic acid is 1:4.

Alternatively hydrophilic additives may be added to the coacervates or biomaterials of the present invention to provide desirable characteristics, such as expedite delivery of the drugs or facilitate the addition of other hydrophilic substances. Exemplary hydrophilic additives useful to shorten the release duration of the pharmacologically active agent include but are not limited to, salts, such as sodium chloride; and amino acids, such as glutamine and glycine.

Other additive materials that may be incorporated into the biocoacervates or biomaterials of the present invention to provide enhanced features include, but are not limited to, insoluble proteins (e.g. collagen, elastin . . . ), ceramics, bioceramics, glasses, bioglasses, glass-ceramics, resin cement, resin fill; more specifically, glass ionomer, calcium sulfate, $Al_2O_3$, tricalcium phosphate, calcium phosphate salts, sugars, lipoproteins, starches, ferrous salts and compounds, carbohydrates, salts, polysaccharides, carbon, magnetic particles, fibers or other magnetic substances, humectants or mucoadhesive enhancers such as glycerol and alginate, absorption or membrane permeation enhancers such as ascorbic acid, citric acid and Lauroylcarnitine. Additional other materials that may be incorporated into the coatable composition include alloys such as, cobalt-based, galvanic-based, stainless steel-based, titanium-based, zirconium oxide, zirconia, aluminum-based, vanadium-based, molybdenum-based, nickel-based, iron-based, or zinc-based (zinc phosphate, zinc polycarboxylate).

Additionally other biocoacervate or biomaterial embodiments include a biocoacervate or biomaterial device that has incorporated into it a marker system that allows the device to be located and imaged using ultrasound, MRI, X-Ray, PET or other imaging techniques. The image marker can be made with air bubbles or density materials that allow easy visualization of the device by ultrasound. The incorporated materials can be metallic, gaseous or liquid in nature. Specific materials that may be utilized as image markers incorporated into the biocoacervate or biomaterial devices include, but are not limited to, Gd-DPTA. It may be possible to cause the biocoacervate or biomaterial to react to an imaging technique, i.e., ultrasound to make bubbles or through the addition of another chemical or substance to the system (e.g., peroxide addition to a biocoacervate or biomaterial that contains peroxidase as an intrauterine marker that can be monitored by ultrasound). Also, the addition of a harmless unique salt solution, or enzyme, may promote gas production by the biocoacervate or biomaterial as an ultrasound maker. The biocoacervate or biomaterial of the present invention can contain agents that can be seen by ultrasound, MRI, PET, x-ray or any imaging device that is either known, in development or developed in the future.

The additives may be added at any time during the preparation of the coacervate or biomaterial. For example additives, such as particles or fibers (drugs, insoluble proteins, hydroxy apetite . . . ), macromolecules (DNA, proteins, peptides, glycosaminoglycans (e.g. hyaluronic acid, chondroiten sulfate) . . . ), small molecules (NSAIDS, Sufentanil, Sirolimis, Paclitaxel, Estradiol, Capsaicin . . . ), combinations thereof and the like may be added to the protein solution or may be added to the molten coacervate. Such addition has the benefit of distributing the additive homogeneously throughout the coacervate or biomaterial.

If additives are to be incorporated into the coacervates or biomaterials of the present invention, they will preferably be included in an amount so that the desired result of the additive is exhibited. Generally, if included in embodiments of the biocoacervate of the present invention, the amount of additives may vary between from about 0.001% to about 60%, preferably from about 0.05% to 30% by weight, and most preferably from about 0.1% to 10% by weight based upon the weight of the biocoacervate or biomaterial.

One method of producing the coacervate of the present invention is by providing one or more selected soluble or solubilized primary proteins, such as collagen, laminin or fibronectin and, in various embodiments, one or more soluble or solubilized secondary proteins such as elastin or albumen. The primary and secondary proteins are added to a sufficient amount of biocompatible solvent, preferably water, under heat until the proteins are substantially dissolved in the solvent. The proteins are added to the solvent that is generally heated to approximately 30-150° C., preferably 40-90° C., and most preferably 40-70° C. thereby producing a protein solution. Once the protein solution is formed, one or more glycosaminoglycans, such as heparin or chondroitin sulfate are added to the protein solution thereby forming an amorphous coacervate, which drops out of the solution. It is noted that before adding the one or more glycosaminoglycans to the protein solution one or more other materials (pharmacologically active agents, additives, etc.) may be added to the one or more heated solvents (water) while stirring. It is also noted that the secondary proteins may dissolve in a solution separate from the primary protein (e.g. the same solution as the glycosaminoglycan) and added to the primary protein solution prior to or with the solution including the glycasaminoglycan. Once the coacervate has dropped out of solution, the solution and coacervate are normally allowed to cool to between 0-35° C., preferably 10-25° C., most preferably 17-22° C. and the solution is poured off the coacerate or the coacervate is extracted from the solution.

Figure 3:
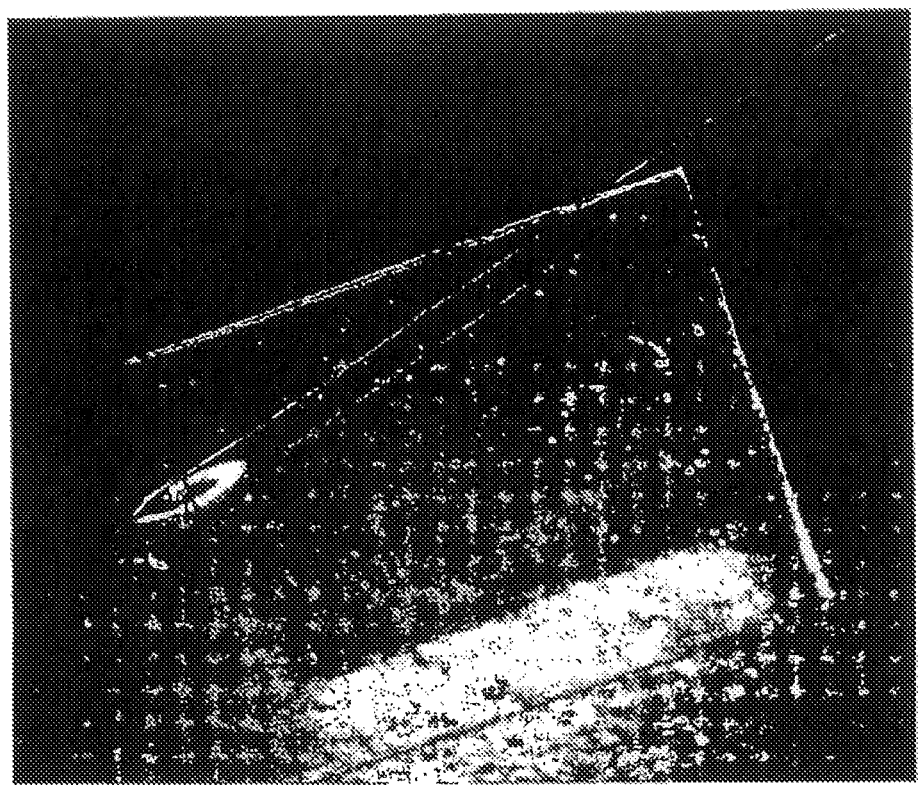
FIG. 3 depicts one embodiment of the biocoacervate of the present invention cut into a square shape.

Many embodiments of the biocoacervate and biomaterials of the present invention are thermoplastics, thereby possessing thermoplastic chemical and mechanical characteristics. Therefore, the biocoacervates and some embodiments of the biomaterials have the property of softening when heated and of hardening again when cooled; these thermoplastic materials can be remelted and cooled time after time without undergoing any substantial chemical change. In view of these thermoplastic characteristics, various embodiments of the formed biocoacervate may be reformed into any shape and size by simply heating the biocoacervate until it melts and forms a liquid. The melted biocoacervate may also be utilized to coat devices or materials. Generally, the biocoacervate can be melted at a temperature between 20-120° C., preferably 25-80° C., most preferably 30-65° C. Next, the melted biocoacervate may be poured into a cast or mold or spray or dip coated onto a device or material and allowed to cool, thereby resolidifying and reforming into the desired shape and/or size. FIG. 3 depicts an example of the biocoacervate of the present invention formed into a square shape. It is noted that at high levels of crosslinking the thermoplastic characteristics of some of the embodiments of the present invention may diminish.

It is noted that in forming the protein solution, the primary and secondary proteins, the biocompatible solvent(s), and optionally the pharmacologically active agent(s) and additive(s) may be combined in any manner. For example, these components may simply be combined in one step, or alternatively, the primary and secondary protein materials may be dissolved in one or multiple biocompatible solvents and an additional protein material, pharmacologically active agent and/or additive may be dissolved and/or suspended in the same or another biocompatible solvent. Once the components are placed into one or more solutions, the resulting solutions may be mixed to precipitate the amorphous biocoacervate.

Once the coacervate is formed, it may be optionally pressed or vacuumed to further form, modify, set the configuration and/or remove any excess solvent or air trapped within the biocoacervate. It is noted that the resulting coacervate may be melted and placed in vacuum to remove any excess air trapped within the coacervate. The pressing may also be performed when a melted coacervate is resetting to a solid state by pouring the melted coacervate in a mold and applying pressure while cooling. The biocoacervate may optionally be dried to reduce water content to transform the coacervate gel-like structure into more of a cohesive body material to allow it to accept compression. Any manually or automatically operable mechanical, pneumatic, hydraulic, or electrical molding device capable of subjecting the coacervate to pressure is suitable for use in the method of the present invention. In the production of various embodiments of the present invention, a molding device may be utilized that is capable of applying a pressure of from about 100 pounds per square inch (psi) to about 100,000 psi for a time period of about one (1) seconds to about forty-eight (48) hours. Preferably, the molding device used in the method of the present invention will be capable of applying a pressure of from about 1000 psi to about 30,000 psi for a time period of from about two (2) seconds to about sixty (60) minutes. More preferably, the molding device used in the method of the present invention will be capable of applying a pressure of from about 3,000 psi to about 25,000 psi for a time period of from about three (3) seconds to about ten (10) minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available. See U.S. Pat. No. 6,342,250 and U.S. application Ser. No. 09/796,170, which are incorporated by reference herein, for a description of one type of compression molding device that may be utilized in the process of the present invention.

As previously indicated, the biocoacervate of the present invention is not soluble in water at room temperature. However, the coacervate does dissolve in saline solution or other physiological solutions. A biocoacervate or biomaterial that does not dissolve in saline solution or other physiological solutions may be produced by setting the biocoacervate in the desired configuration and size by utilizing a crosslinking technique. It is also noted that various crosslinking reagents, techniques and degrees of crosslinking manipulate the melting point of the crosslinked material and its physical and biological characteristics. It has been found that the application of crosslinking to the biocoacervate will generally tend to raise the melting point of the biocoacervate.

Many crosslinking techniques known in the art may be utilized to set the biocoacervate into the desired configuration, thereby forming a biomaterial that does not dissolve in saline solution. For example, embodiments of the biocoacervate may be crosslinked by reacting the components of the biocoacervate with a suitable and biocompatible crosslinking agent. Crosslinking agents include, but are not limited to glutaraldehyde, p-Azidobenzolyl Hydazide, N-5-Azido-2-nitrobenzoyloxysuccinimide, 4-[p-Azidosalicylamido]butylamine, glycidyl ethers such as 1,4-butandiol diglycidylether, any other suitable crosslinking agent and any combination thereof. A description and list of various crosslinking agents and a disclosure of methods of performing crosslinking steps with such agents may be found in the Pierce Endogen 2001-2002 or 2003-2004 Catalog which is hereby incorporated by reference. It is also noted that multiple applications of crosslinking agents at different stages may produce desired products. For example, crosslinking the biocoacervate after initial formation and then again following particle formation of the biocoacervate has proven effective.

Furthermore, it is noted that embodiments of the coacervates of the present invention may include crosslinking reagents that may be initiated and thereby perform the crosslinking process by UV light activation or other radiation source, such as ultrasound or gamma ray or any other activation means.

The protein biocoacervate may also be crosslinked by utilizing other methods generally known in the art. For example, the coacervates of the present invention may be partially or entirely crosslinked by exposing, contacting and/or incubating a coacervate with a gaseous crosslinking reagent, liquid crosslinking reagent, light, heat or combination thereof. In various embodiments of the present invention the coacervate may be crosslinked by contacting the coacervate with a liquid crosslinking reagent, such as glutaraldehyde or 1,4-butandiol diglycidylether. In one preferred embodiment of the present invention the coacervate is crosslinked in a solution of between 0.01%-50% gluteraldehyde. Additionally, it is noted that in processes including a crosslinking agent the coacervate is generally exposed to the crosslinking agent for a period of 1 min to 24 hours, preferably between 5 min. and 6 hours and more preferably between 15 min. and 3 hours.

Embodiments of the present invention may also include the addition of reagents to properly pH the resulting coacervate, biomaterial and related devices of the present invention. These pH reagents may be added to the coacervate during formation of the coacervate, exposing the formed coacervate to a solution of the desired pH or adjusting the pH when the coacervate is in a melted state. The appropriate adjustment of pH thereby enhances the biocompatible characteristics of the biomaterials with the host tissue of which it is to be administered and may also act to stabilize the material in physiologic conditions. When preparing the coacervate, the pH reagents are generally added to the protein solution prior to addition of the glycosaminoglycans. However, the pH reagent may alternatively be added after the amorphous coacervate is formed. For example the pH reagent may be added to the melted form of the coacervate in the attempt to obtain the proper pH levels. In various embodiments of the present invention, the adjustment of pH can be performed by the addition of drops of 0.05N to 4.0N acid or base to the protein solution or melted coacervate until the desired pH is reached as indicated by a pH meter, pH paper or any pH indicator. More preferably, the addition of drops of 0.1N-0.5N acid or base are used. Although any acid or base may be used, the preferable acids and bases are HCl and KOH, NaOH or combinations thereof, respectively. It has been found that adjusting the pH at or between 4 and 9, and in many embodiments at or between 6 and 8, have provided beneficial materials.

The resulting biocoacervate preferably has the maximum solvent amount absorbable with as little excess solvent as possible while still being structured into a shape-holding amorphous solid and possessing the desired features relevant to the material's and/or device's function, e.g., preferably a solvent content of from about 20% to about 90%, more preferably a solvent content of from about 30% to about 80% and most preferably 40% to 75%. Additionally, the amount of proteins and glycosaminoglycan found in the resulting coacervate or biomaterial may vary between from about 10% to about 80%, in some embodiments from about 20% to 70% by weight, and in other embodiments from about 25% to 60% by weight based upon the weight of the resulting biocoacervate or biomaterial. The amount of glycosaminoglycan present in various embodiments of the present invention generally is about 3% to about 25%, in some embodiments about 5% to 20% by weight, and in other embodiments about 8% to 15% by weight based upon the weight of the protein included in the biocoacervate.

Since biocompatible proteins and solvents are used in the manufacture of the biocoacervates, biomaterials and related devices of the present invention, the potential for adverse tissue reactions to foreign substances, such as chemical solvents are reduced, if not substantially precluded. For all of these reasons, the coacervates and biomaterials in accordance with the present invention may advantageously be used to effect a local therapeutic result in a patient in need of such treatment. More specifically, the biocoacervates and biomaterials of the present invention may be injected, implanted, or administered via oral, sublingual, mucosal, as well as nasal, pulmonary, subcutaneous, intradermal or any parenteral modes of delivery. Moreover, the coacervates or biomaterials may be delivered to a site within a patient to illicit a therapeutic effect either locally or systemically. For example, depending on the desired therapeutic effect, the coacervates or biomaterials may be used to regenerate tissue, repair tissue, replace tissue, and deliver local and systemic therapeutic effects such as analgesia or anesthesia, or alternatively, may be used to treat specific conditions, such as coronary artery disease, heart valve failure, cornea trauma, neural tissue defects or trauma, skin wounds, burned skin, bone defects and trauma, ligament defects and trauma, cartilage defects and trauma wrinkles and other tissue specific conditions. The coacervates or biomaterials that include pharmacologically active agents may be utilized in instances where long term, sustained, controlled release of pharmacologically active agents is desirable, such as in the treatment of surgical and post-operative pain, cancer pain, or other conditions requiring chronic pain management.

The patient to which the coacervates or biomaterials are administered may be any patient in need of a therapeutic treatment. Preferably, the patient is a mammal, reptile or bird. More preferably, the patient is a human. Furthermore, the coacervates or biomaterials can be implanted in any location to which it is desired to effect a local therapeutic response. For example, the coacervates, biomaterials or related devices may be administered, applied, sutured, clipped, stapled, gas delivered, injected and/or implanted vaginally, in ova, in utero, in uteral, subcutaneously, near heart valves, in periodontal pockets, in the eye, in the intracranial space, next to an injured nerve, next to the spinal cord, intradermally etc. Furthermore, implanted coacervates, biomaterials or related devices may absorb water and swell, thereby assisting the coacervates, biomaterials or related devices to stay substantially in the location where it was implanted or injected.

The present invention will now be further described with reference to the following non-limiting examples and the following materials and methods were employed. It is noted that any additional features presented in other embodiments described herein may be incorporated into the various embodiments being described.

Drug Delivery Devices and Tissue Fillers:

As previously suggested, various embodiments of the biocoacervates and biomaterials of the present invention may be utilized as drug delivery devices or tissue fillers. A drug delivery device or tissue filler produced and administered as previously disclosed or suggested includes the biocompatible features of the components of the biocoacervate or biomaterial and thereby reduces or prevents the undesirable effects of toxicity and adverse tissue reactions that may be found in many other types of drug delivery devices. Furthermore, the controlled release characteristics of this type material provides for a higher amount of pharmacologically active agent(s) that may be incorporated into the biocoacervate or biomaterial. The controlled release of pharmacologically active agent, if present, is partially attributed to the homogenous distribution of the pharmacologically active agent(s) throughout the biocoacervate or biomaterial. This homogenous distribution provides for a more systematic, sustainable and consistent release of the pharmacologically active agent(s) by gradual degradation of the coacervate or material or by diffusion of the pharmacologically active agent(s) out of the coacervate or material. As a result, the release characteristics of the pharmacologically active agent from the biocoacervate, biomaterial and/or device are enhanced.

Additionally, as previously mentioned, other optional biocompatible additives, if included in the coacervate or biomaterial, will be compelled and influenced to interact with the various components, including the pharmacologically active agents if present, to augment their biodurability, biocompatibility and/or drug release characteristics if drugs are present in the materials. Augmentation may include inhibiting or enhancing the release characteristics of the pharmacologically active agent(s), if present. For example, a multi-layered drug delivery device may comprise alternating layers of biocoacervates or biomaterials that have sequential inhibiting and enhancing biocompatible additives included, thereby providing a pulsing release of pharmacologically active agents. A specific example may be utilizing glutamine in a layer as an enhancer and polyanhydride as an inhibitor. The inhibiting layer may include drugs or no drugs.

The drug delivery devices or tissue fillers of present invention may be formed into any shape and size, such as a cylinder, a tube, a wafer, particles or any other shape that may optimize the delivery of the devices or fillers and optionally the incorporated pharmacologically active agents included therein. For example, the composite coacervate or biomaterial may be processed into particles for subsequent administation as a therapeutic device such as a tissue filler or drug delivery device.

Figure 4A:
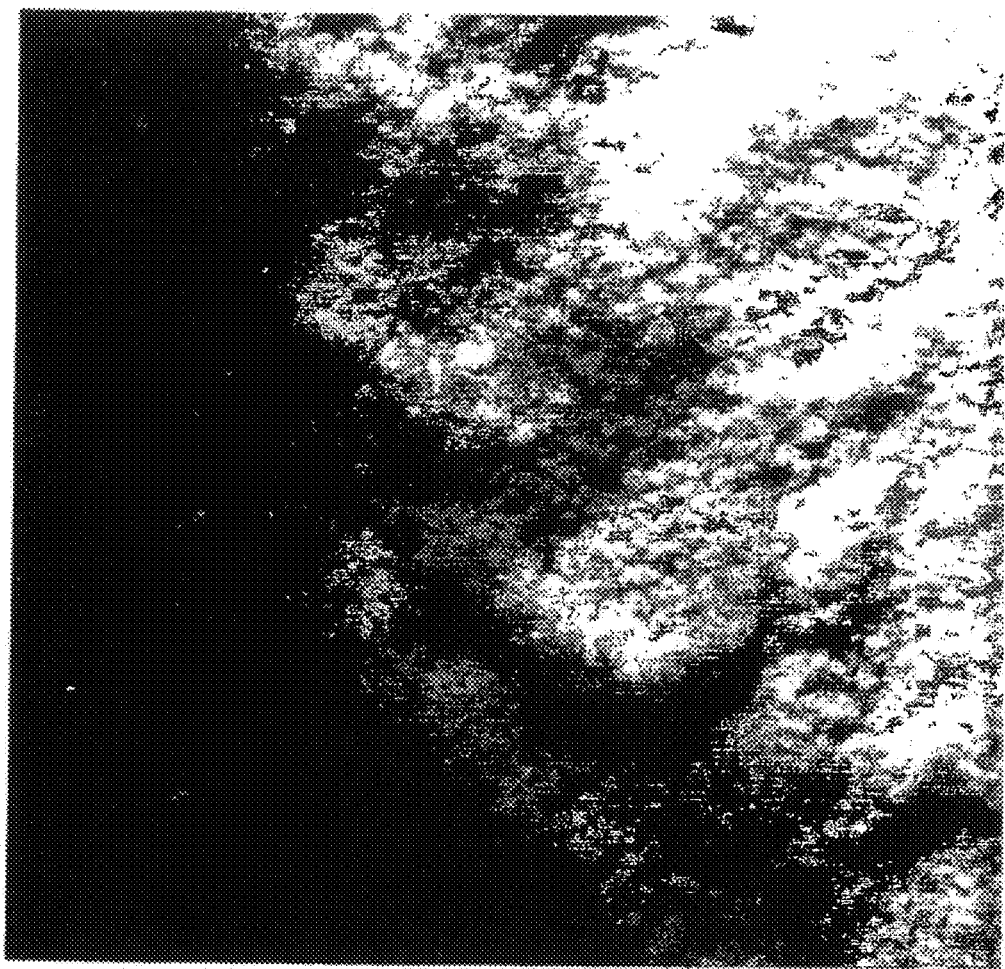
FIG. 4A depicts one embodiment of the particles of the present invention.
Figure 4B:
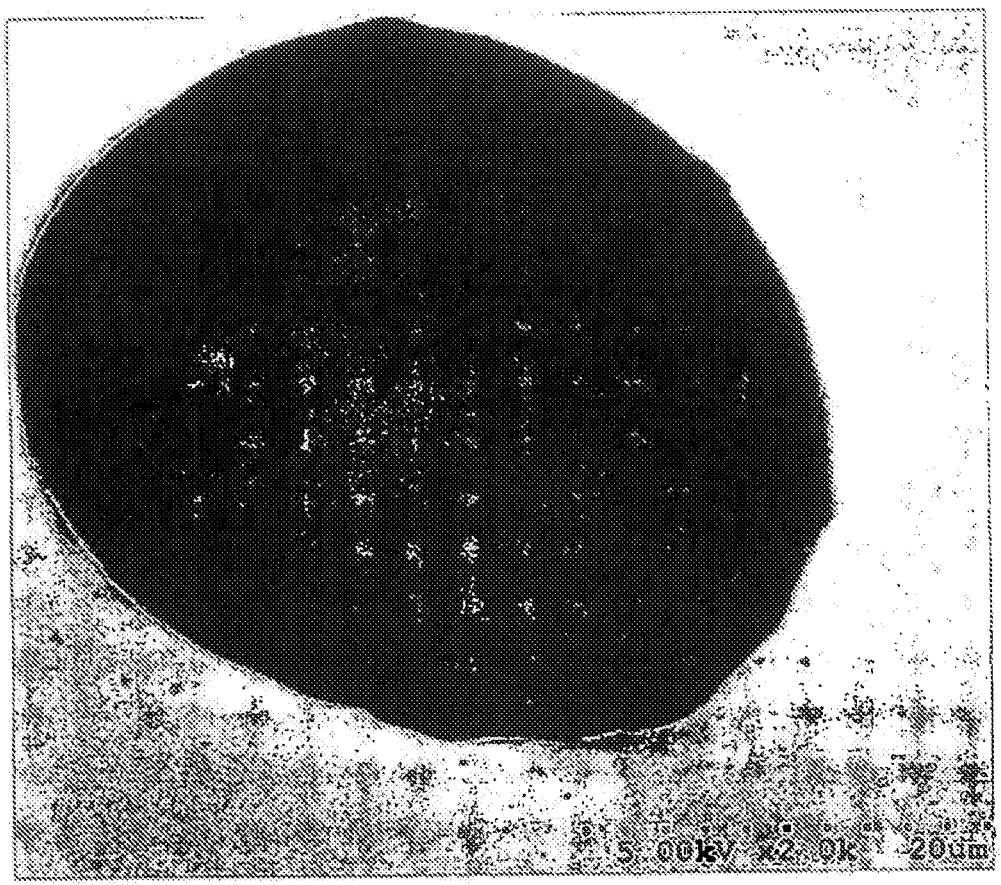
FIG. 4B depicts one embodiment of a particle of the present invention illustrated using frozen sample scanning electron microscopy.

An illustration of an embodiment of the particles of the present invention is depicted in FIG. 4A. In one embodiment of the present invention the particles are produced utilizing the biocoacervate or biomaterial of the present invention as previously described. Methods of producing the particles utilized in products of the present invention includes crushing, cutting, pulverizing, homogenizing or grinding of the biocoacervate or biomaterial in either wet or dry conditions until the particles are formed. The particle formation process may be performed with the biocoacervate or biomaterial in its original state or after applying heat, freeze drying techniques such as liquid nitrogen freeze drying or dry ice freeze drying, vacuum or other similar drying techniques to eliminate excess solvent from the biocoacervate or biomaterial. Various particle embodiments of the present invention are substantially insoluble thereby allowing them to be integrated and remodeled by the host tissue rather than be consumed and excreted. FIG. 4B depicts a single particle of one embodiment of the biocoacervate of the present invention illustrated using frozen sample scanning electron microscopy.

One example of an alternative method to make particles is by homogenizing a crosslinked coacervate thereby producing particles. In such a method a block or other shape of the coacervate may be crosslinked with a crosslinking agent, such as 0.01M to 10M gluteraldehyde or 1,4-butandiol diglycidylether. Once crosslinked the biocoacervate is next placed in a homgenizer and cut into particles. One or more additional crosslinking steps may be performed after homogenization of the coacervate by exposing the particles to a second solution including one or more crosslinking agents, such as gluteraldehye, formaldehyde, glyoxal or 1,4-butandiol diglycidylether. It is noted that alternative crosslinking solutions and conditions (e.g. pH, temperature, solvents . . . ) may be utilized for the extra crosslinking steps.

Generally, the particles may vary in size but are normally approximately 10 nm-5 mm, preferably 500 nm-2.5 mm and more preferably 1-1000 μm. A characteristic of the particles produced from the biocoacervate material is that they no longer aggregate when in the particulate state. Furthermore, prior studies have demonstrated that the particles do not aggregate in saline and are easily delivered through small gauge needles, such as 27 or 30 guage needles. The particles can be made to disassociate at very slow or fast rates in aqueous solutions.

After the particles are formed using the various methods described above, they are characterized for their basic structure. First the particles may be segregated using a series of pharmaceutical drug sieves.

In various embodiments of the present invention, the particles may be utilized as a drug delivery device or a tissue filler by administering them subcutaneously or intradermally to the patient by a variety of administration techniques known in the art. One such administration procedure of the present invention comprises a syringe injection of such particles or a slurry of such particles into the desired site. Saline is a solution that may be employed to prepare such a slurry, but any biocompatible solution may be utilized. Also, lubricants, such as polyvinylalcohol, polyethylene glycol, dextran, proteins (human, bovine, porcine, or equine) such as collagen, elastin, albumen, proteoglycans or glycans, hyaluronic acid, lipids, oils or any other lubricious agent, may be added to the particles or slurry to facilitate injection of the particles through a needle syringe assembly. These lubricants assist in facilitating the administration of the particles through the applicator, such as a syringe and also may be made to act as an immunogenic mask, thereby reducing potential inflammatory and/or immune responses. In various embodiments of the present invention the lubricants may comprise approximately less than 5% and preferably less than 1% of the particle or slurry contents. Saline has been selected for the initial material for several reasons including its common use in medical procedures and its availability in a sterile form.

Figure 5:
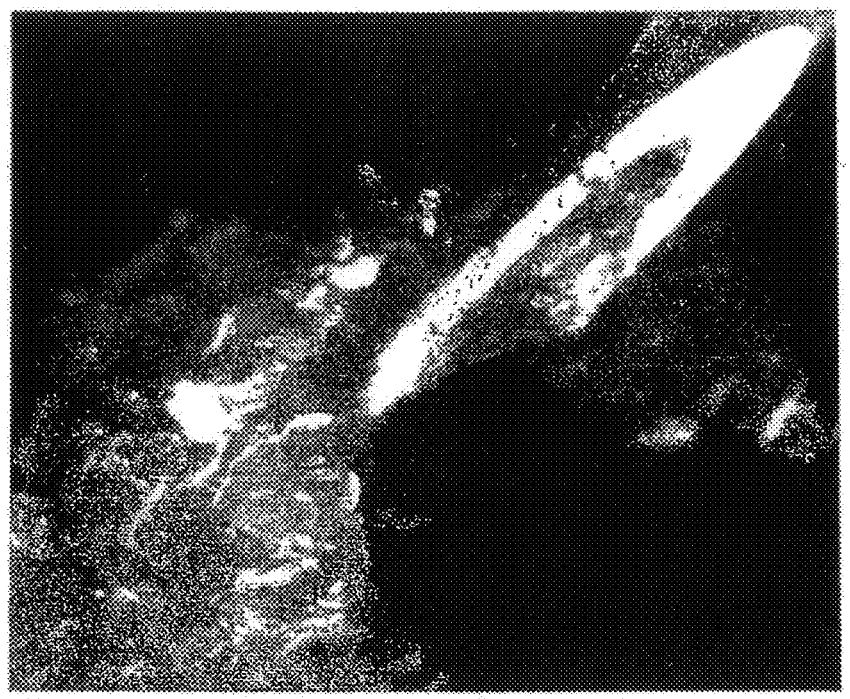
FIG. 5 depicts one embodiment of the particles of the present invention wherein a slurry of particles and saline are delivered through a 27 guage needle.

The particles or particle slurry may be delivered in any way known in the art including delivery through a needle, air-gun, iontophoresis, spray bottle, etc. Any gauge needle may be utilized to deliver the slurry containing the particles of the present invention, including but not limited to 12-30 gauge needles. FIG. 5 depicts one embodiment of the particles of the present invention wherein a slurry of particles and saline are delivered through a 27 guage needle. It is noted again that the particles may optionally include one or more pharmacologically active agents. However, a suitable tissue filler may comprise a protein coacervate material without the presence of pharmacologically active agents.

Alternatively, the particles of the present invention may also be placed into position without utilizing needles, such as when the particles are too large to fit through a needle. These particles are typically 0.5-5 mm in size, more typically 1-25 mm. In such a procedure the particles may be surgically implanted and packed into and/or around the injured site. For example, particles may be surgically packed into and around an injured or vacant area and subsequently sealed into position by the host tissue surrounding the injured area, such as a fractured bone. The injection or implantation of biocompatible particles of the present invention allows for the particles to remodel with and/or resorb into the surrounding tissue or remain positioned in the injured or vacant area after it has mended or healed.

Also, various embodiments of particles of the present invention may be administered as a drug delivery device orally or through the mucosal tissue. For example a particle loaded saline solution may be administered as a nasal spray to deliver one or more pharmacologically active agents. The spray may be similar to the slurry previously described, but may likely include a lower concentration of particles to saline compared to the slurry prepared for injection. This type of particulate solution may be administered by any means known in the art, such as a nasal spray bottle or an inhaler.

Finally, additional embodiments of biocoacervate drug delivery devices of the present invention includes the production of therapeutic devices and/or medical device coatings utilizing the biocoacervate of the present invention. For example, the biocoacervate of the present invention may be formed into a drug delivery device or wound healing device in the form of a cylinder, wafer, particles, capsule for inclusion of drug or any other suitable shape or design. The shape of the delivery device may be formed by any device known in the art, such as a conventional pill press, molds, casts or any of the molding or shaping devices known in the art. For example a drug delivery device or wound healing device comprising one or more proteins, such as collagen, keratin, laminin, fibronectin, silk, silk fibroin, actin, myosin, fibrinogen, thrombin, aprotinin, elastin and/or albumen, one or more glycosaminoglycans such as heparin, one or more biocompatible solvents such as water, DMSO, ethanol and/or glycerol and one or more pharmacologically active agents, such as ibuprofen, capsaicin, fentanyl, benzocaine, botox, acetaminophen or desmopressen may be produced. In one example, a delivery device can be adhered to the inside of the mouth or nose by simply applying or pressing the device, such as a wafer or particles, to the mucosal tissue. The device will generally deliver the drug through the mucosal tissue without losing drug orally.

Also, a release mechanism may be included in the biocoacervate or biomaterial for the release of the one or more pharmacologically active agents. The release mechanism may be a material that encapsulates a larger drug delivery device, such as a cylinder or the release mechanism may be within the coacervate or biomaterial that includes encapsulated particles of either the drug delivery device or particles of one or more pharmacologically active agents. Additionally, the coacervate or biomaterial of the present invention may also encapsulate a drug delivery device larger and/or different than a particle that is covered by the release mechanism material.

Figure 6:
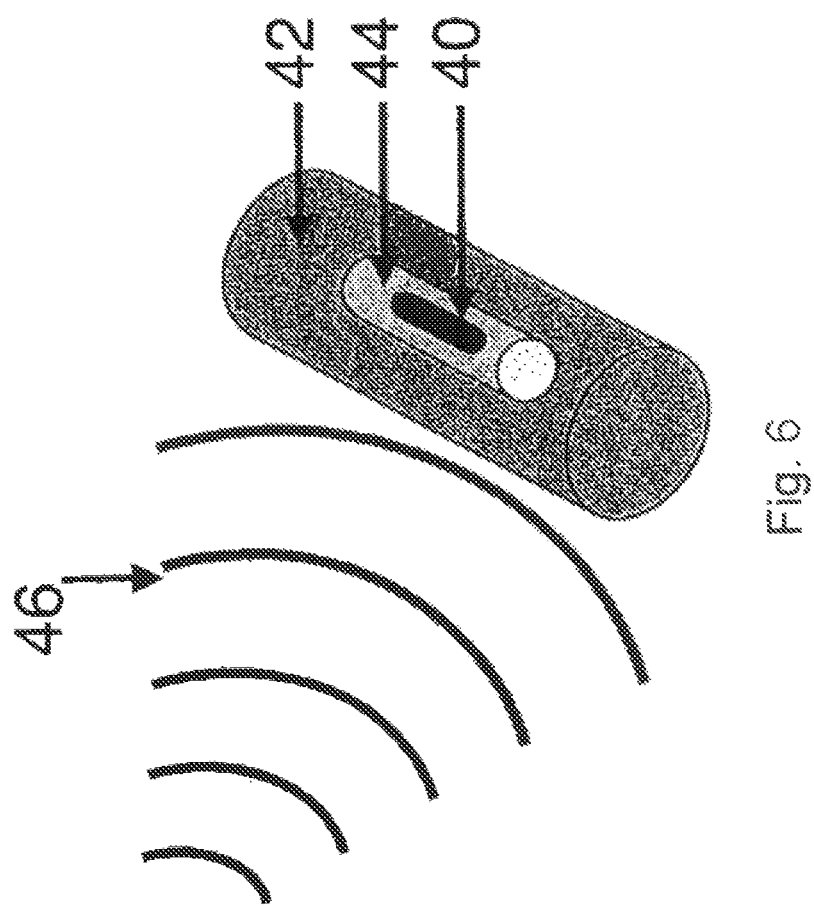
FIG. 6 depicts a biomaterial drug delivery device that include release mechanisms contained in the biomaterial.

FIG. 6 depicts an embodiment of a drug delivery device that includes a release mechanism. The release mechanism 40 is positioned within a biocoacervate or biomaterial 42. Generally, the mechanism 40 is a material that creates a shell around the pharmacologically active agents 44 and inhibits their release until opened by some outside stimuli 46. Normally, the pharmacologically active agent can be released by a pulse of energy, radiation or a chemical reagent acting upon the encapsulating substance. For example, a drug delivery device comprising a pharmacologically active agent encapsulated in a polyanhydride coating inhibits release of the pharmacologically active agent and/or its interaction with the host tissue. In this example, the pharmacologically active agents can be released when the polyanhydride surface is contacted with an energy pulse, such as an ultrasound pulse. Such an embodiment has many advantages in treating afflictions that may require an extended time period before release of the pharmacologically active agent is necessary.

Treatment of cancer or chronic pain may be examples of afflictions that may benefit from such an embodiment. The retention of chemotherapy drugs localized in an area of the patient that includes cancerous tissue may be beneficial to the long term treatment of the patient. The treatment may include implantation of a drug delivery device that includes a release mechanism in a position of the body wherein cancerous tissues has been previously resected. Upon determination that cancerous cell growth may be ongoing or occurring again, the drug delivery device can be released by some stimuli, such as a ultrasound pulse or chemical reagent. The stimuli opens the release mechanism material and allows the host tissue to interact with the pharmacologically active agents.

Encapsulated or Coated Stents and Medical Devices:

Other embodiments of the present invention include the utilization of the biocoacervates or biomaterials to encapsulate or coat stents or other medical devices. A valuable attribute of such coatings is the hemocompatiblity of these biocoacervates and biomaterials. The biocoacervates or biomaterials of this invention can be used to coat the surface of a variety of implantable devices, for example: drug-delivering vascular stents (e.g., self-expanding stents typically made from nitinol, balloon-expanded stents typically prepared from stainless steel); other vascular devices (e.g., grafts, catheters, valves, artificial hearts, heart assist devices); implantable defibrillators; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices), urological devices (e.g., penile, sphincter, urethral, bladder and renal devices, and catheters); colostomy bag attachment devices; ophthalmic devices (e.g. intraocular coils/screws); glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts), urinary catheters, intravenous catheters, small diameter grafts, vascular grafts, artificial lung catheters, atrial septal defect closures, electro-stimulation leads for cardiac rhythm management (e.g., pacer leads), glucose sensors (long-term and short-term), degradable coronary stents (e.g., degradable, non-degradable, peripheral), blood pressure and stent graft catheters, birth control devices, BHP and prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Examples of other suitable devices include, but are not limited to, vena cava filters, urinary dialators, endoscopic surgical tissue extractors, atherectomy catheters, clot extraction catheters, PTA catheters, PTCA catheters, stylets (vascular and non-vascular), coronary guidewires, drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

Other examples of medical devices suitable for the present invention include, but are not limited to implantable vascular access ports, blood storage bags, blood tubing, central venous catheters, arterial catheters, vascular grafts, intraaortic balloon pumps, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli (also known as "distal protection devices").

A stent is a tube made of metal or plastic that is inserted into a vessel or passage to keep the lumen open and prevent closure due to a stricture or external compression. Stents are commonly used to keep blood vessels open in the coronary arteries, into the oesophagus for strictures or cancer, the ureter to maintain drainage from the kidneys, or the bile duct for pancreatic cancer or cholangiocarcinoma. Stents are also commonly utilized in other vascular and neural applications to keep blood vessels open and provide structural stability to the vessel. Stents are usually inserted under radiological guidance and can be inserted percutaneously. Stents are commonly made of gold, stainless steel, nitinol or cobalt chromium alloys. However, stents constructed of any suitable material may be utilized with the coacervates or biomaterials of the present invention.

Encapsulation or coating of a stent or other medical device with the coacervates or biomaterials of the present invention produces a device that is more biocompatible with the host tissue than the stent alone. Such encapsulation or coating of the stent or other medical device reduces or prevents adverse immuno-response reactions to the stent device being administered and further enhances acceptance and remodeling of the device by the host tissue. Furthermore, encapsulated or coated stents or medical devices may also include one or more pharmacologically active agents, within or attached to the coacervates or biomaterials that may assist in the facilitation of tissue acceptance and remodeling as well as inhibit additional adverse conditions sometimes related to implantation. For example the release of certain pharmacologically active agents from the biocoacervate or biomaterial coating on a stent, may prevent blockage of a blood vessel due to platelet aggregation, cell proliferation, inflammation or thrombosis. In addition to anti-platelet aggregation drugs, anti-inflammatory agents, gene altering agents such as antisense, antiproliferative agents, angiogenesis inhibitors and other pharmacologically active agents can be administered locally to the host tissue through the biocoacervate coating of the present invention.

The coacervates or biomaterials may completely encapsulate or otherwise coat the exterior of the stent or other medical device. The stent or medical device may be coated or encapsulated with the biocoacervate or biomaterial of the present invention utilizing any coating or encapsulation process known in the art, such as dip coating, spraying, compression molding, casting etc. For example, a stent may be spray coated with one or more embodiments of the present invention while in a melted state; the coating subsequently solidfies around the stent upon cooling. Also, the medical device or stent may be precoated with an adhesive enhancer, such as Parylene to enhance the adhesion of the biocoacervate to the device. In various embodiments of the present invention, the stent or medical device is coated with a coacervate that is subsequently set by utilizing one of the previously described crosslinking techniques. In other embodiments an elastic cover of the biocoacervate or biomaterial may be made to fit over or encapsulate all or part of a medical device, such as pacemaker, valve, or catheter.

Figure 7:
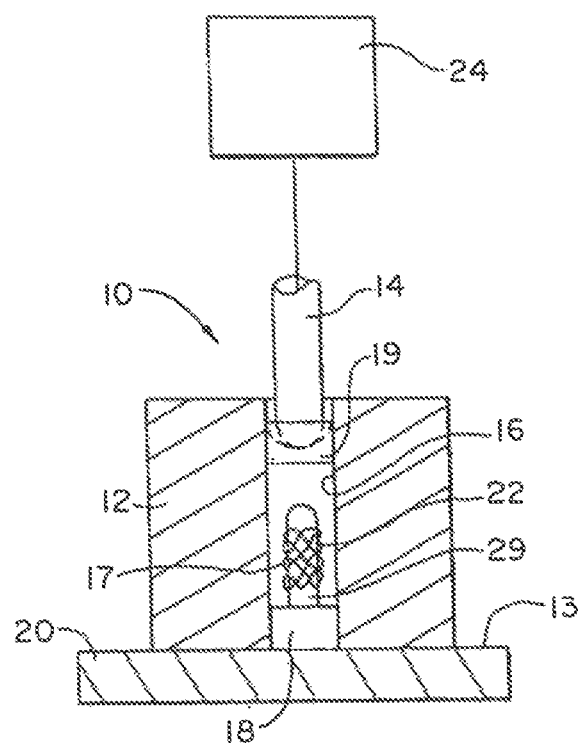
FIG. 7 is a schematic illustration, in partial cross-sectional view, of a compression molding device that may be used in the method of the present invention in wherein the inner insert includes a mandrel that is engaged with a stent.

In one embodiment as depicted in FIG. 7, a compression molding device wherein the inner insert 18 includes a mandrel 29 that extends upward from the insert 18 into the chamber 17 is utilized to coat a stent 32. Following preparation of the coacervate 23, inner insert 18 is inserted into the cavity 16. A stent 32 is positioned over the mandrel 29, the coacervate 23 is melted and subsequently placed in the cavity. Once the stent 32 and coacervate 23 are placed in the cavity 16, they are pressed while cooling to form an encapsulated stent. Encapsulation or coating of the stent 32 is determined by the size of the mandrel 29 utilized in the compression molding device. A stent 32 that fits snuggly over the mandrel 29 will allow for only a coating upon the exterior of the stent 32. A smaller mandrel 29 that does provide a snug fit for the stent 32 will allow biocoacervate material to move between the mandrel 29 and the stent 32 thereby creating an encapsulation of the stent 32. Following compression, the encapsulated or coated stent device is then removed from the compression molding device and crosslinked to set the coacervate and form a biomaterial coated stent. In various embodiments, the stent device, either encapsulated or coated, has a wall thickness of approximately 0.05 mm to 2 mm and preferably has a wall thickness of 0.15 to 0.50 mm.

As previously described additional additives may be included in the coacervates or biomaterials to provide additional structural stability and durability to the encapsulated or coated stent device. In two embodiments, the stent device of the present invention may be produced by preparing a coated stent device that includes a ratio of 1:2:6 heparin to elastin to collagen and 1:2:6 condroitin sulfate to elastin to collagen.

Furthermore, the coacervates and biomaterials used to coat stent devices can also be used to incorporate peptides and other materials that have the ability to inhibit cell migration. A disadvantage of utilizing stents in a vessel is that the expansion of the vessel upon insertion of the stent injures the vessel and may allow smooth muscle cells to enter into the vessels thereby occluding or restenosing the vessel through cellular proliferation. Occlusion of the vessel and restenosis can be treated by utilizing the coated stent device and vessels or tube grafts of the present invention. Vessels and tubular grafts will be explained later in the text of this disclosure. It is important to note that inserting a stent coated with the coacervate or biomaterials of the present invention, with or without drugs, can prevent such breakdown and growth of cells into the diseased or damaged vessel.

Tissue Grafts:

Additional embodiments of the present invention include the utilization of the biocoacervates and/or biomaterials in producing tissue grafts such as vessels; tubular grafts such as tracheal tubes, bronchial tubes, catheter functioning tubes, lung, vertebral discs, gastrointestinal segments; valves; cartilage; tendons; ligaments; skin; pancreatic implant devices; breast implants; tissue fillers, such as void or wrinkle fillers, urinary or sphicter fillers to correct incontinence; other types of tissue that relate to the heart, brain, nerve, spinal cord, nasal, liver, muscle, bone, thyroid, adrenal, pancreas, and surrounding tissue such as connective tissue, pericardium and peritoneum. It is noted that a tube does not necessarily have to be cylindrical in shape, but is generally found in that configuration.

Figure 8:
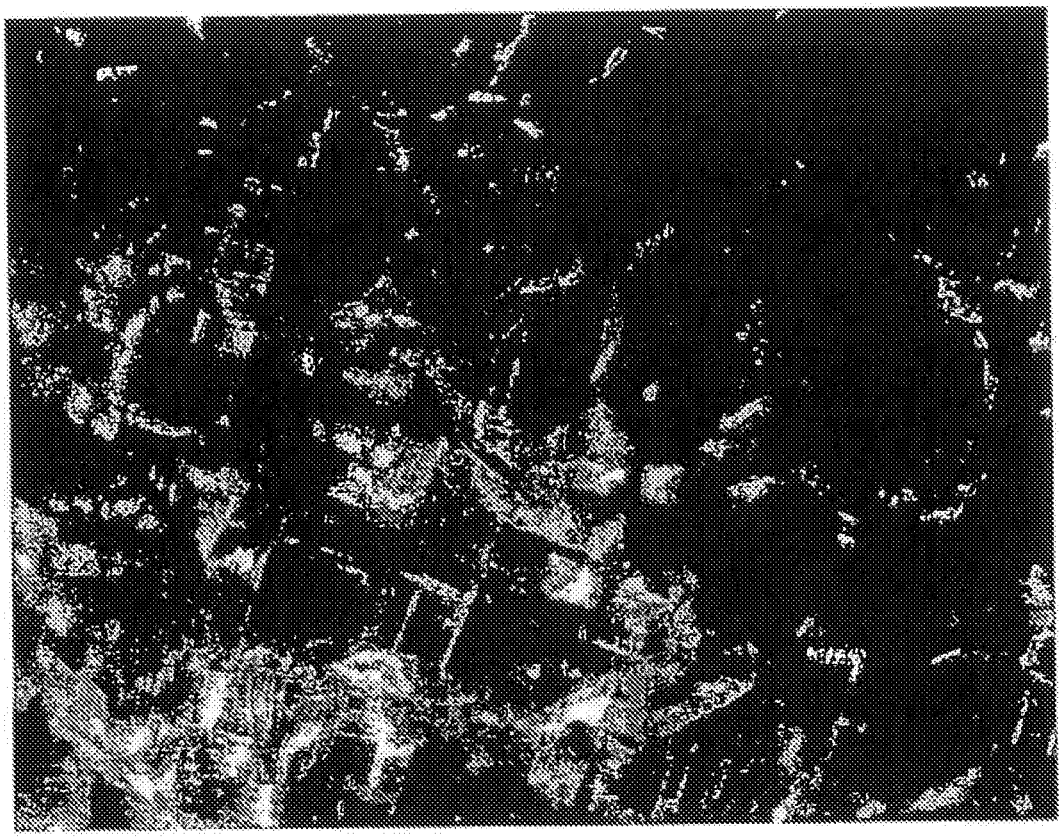
FIG. 8 depicts an embodiment of a polypropylene/polytetrafluoroethylene scaffolding structure before applying the biocoacervate of the present invention.
Figure 9A:
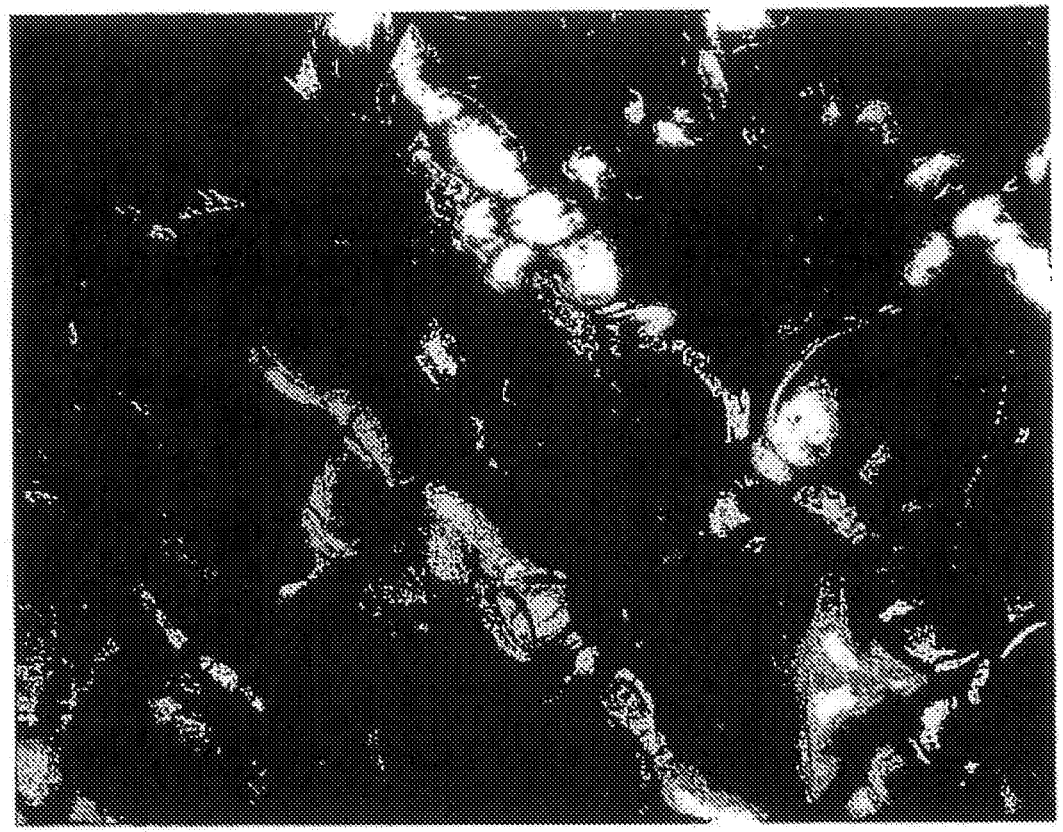
FIGS. 9A-C, depict an embodiment of a polypropylene/polytetrafluoroethylene tube that is coated and impregnated with the biocoacervate of the present invention.
Figure 9B:
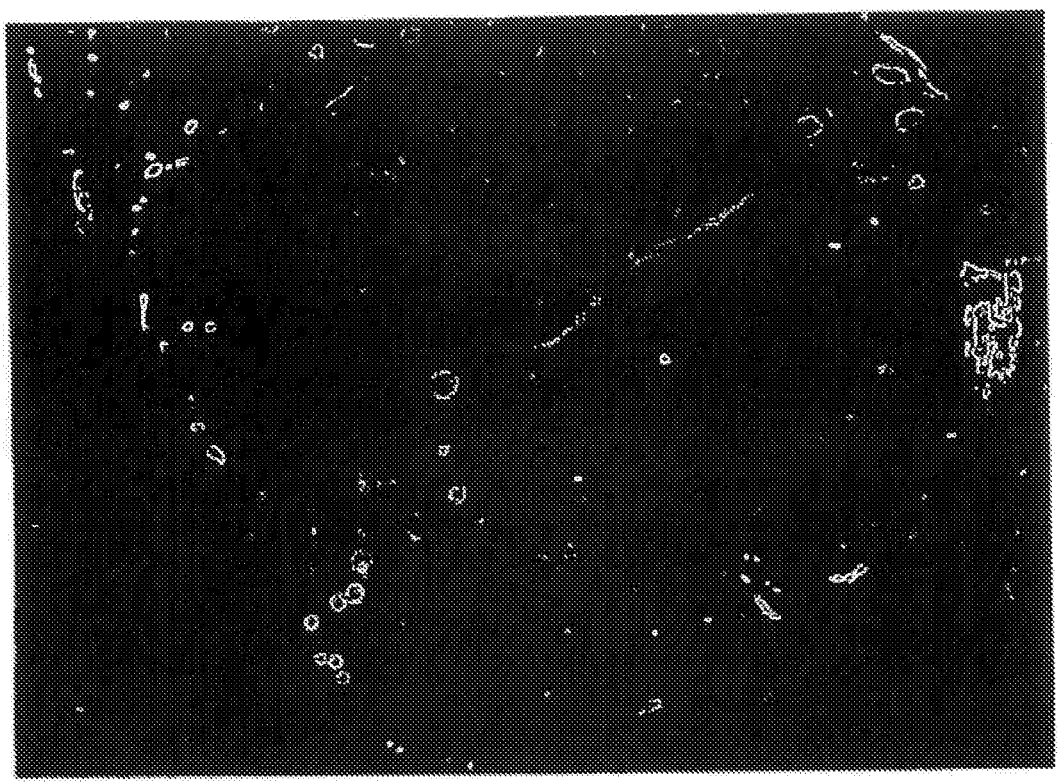
Figure 9C:
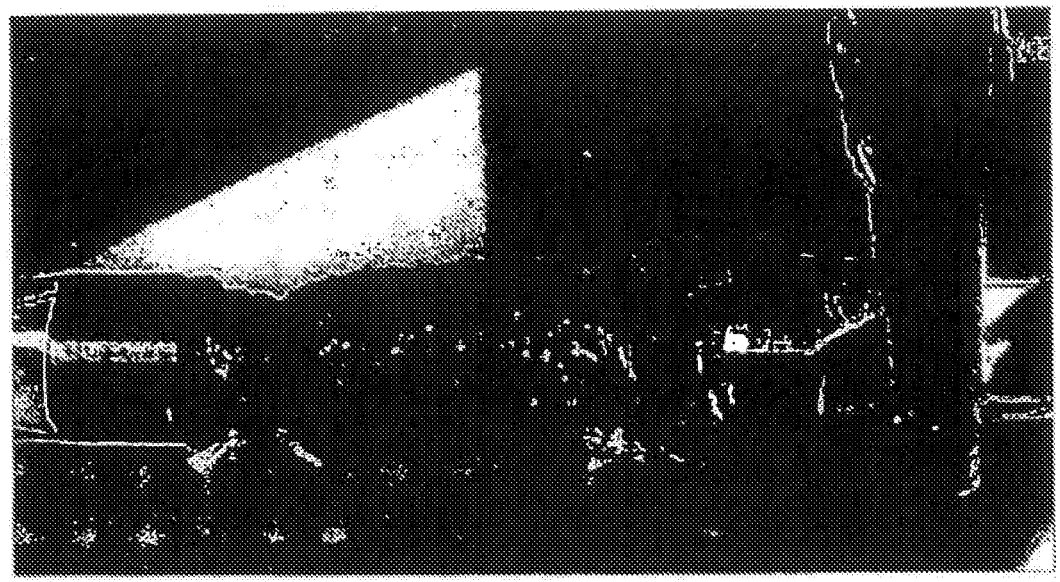

In various embodiments of the present invention the biocoacervate or biomaterial may be coated or impregnated onto or into a scaffolding type structure, such as a polyurethane foam tube, methacrylate meshing or foam, nylon meshing, polypropylene/polytetrafluoroethylene mesh or mesh tube, cotton knitted material, Dacron knitted material, polytetrafluoroethylene, silk and Teflon. FIG. 8 depicts an embodiment of a polypropylene/polytetrafluoroethylene mesh tube, such as that produced by Secant, Inc., before the biocoacervate material of the present invention is applied. In one embodiment of the present invention, as depicted in FIGS. 9A-B, a polypropylene/polytetrafluoroethylene mesh tube, as shown in FIG. 8, is prepared by applying the melted biocoacervate to the tube and supplying vacuum to remove trapped air within the pores of the tube. It is noted that in other embodiments of the present invention, the scaffolding structure of the vessel graft may be a cotton tube or a polyurethane foam tube rather than the a polypropylene/polytetrafluoroethylene mesh tube. Finally, FIG. 9C depicts the vessel graft including a polypropylene/polytetrafluoroethylene mesh tube that has been placed under hydrostatic pressure of over 200 psi for greater than 3 days.

Figure 10A:
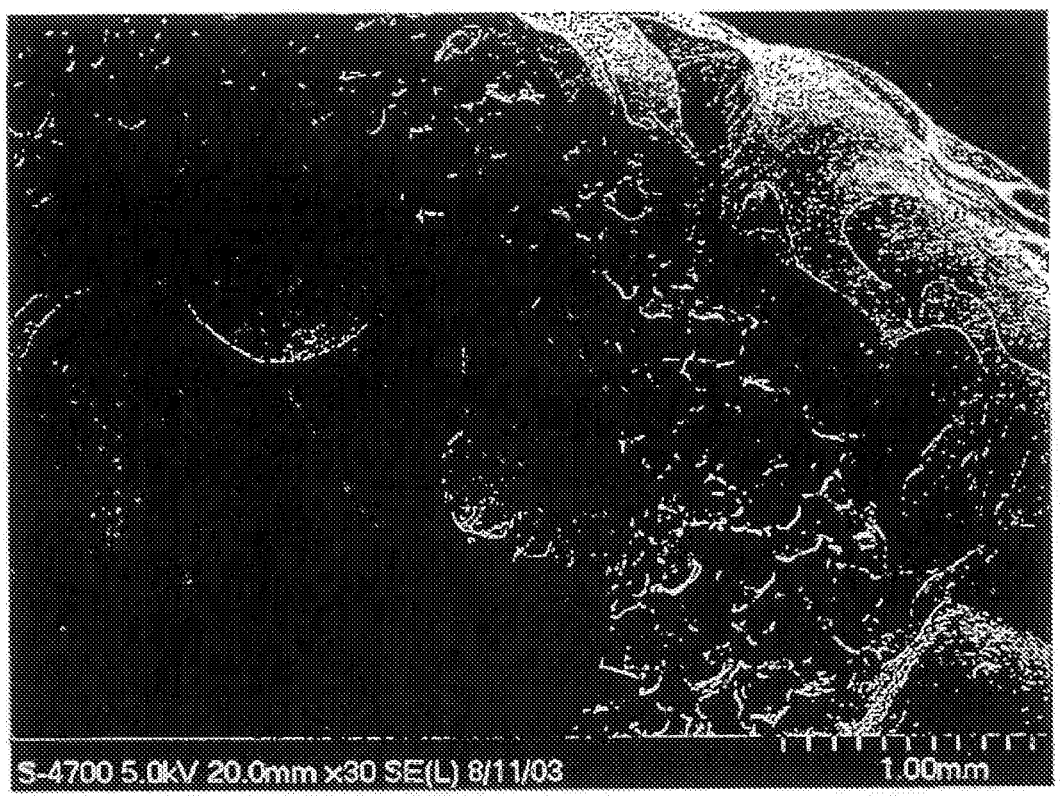
FIGS. 10A-B depict magnified cross-sectional views of one embodiment of a vessel of the present invention wherein the scaffolding material is a polyurethane foam.
Figure 10B:
Figure 11A:
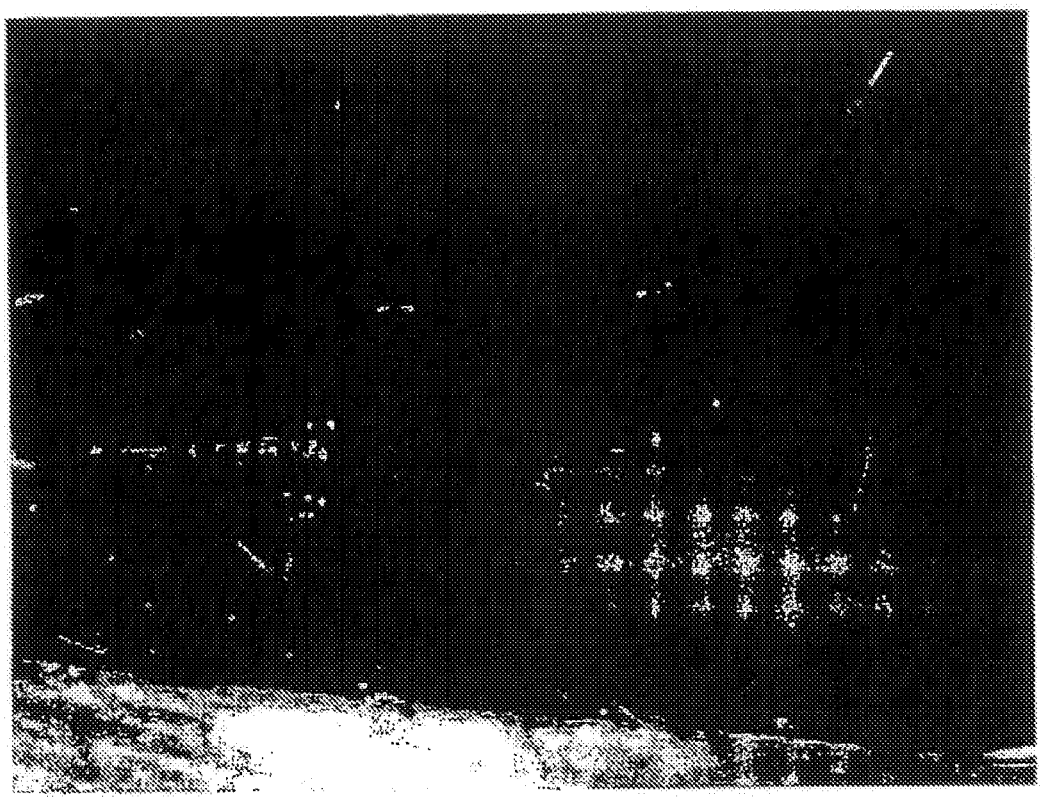
FIGS. 11A-B depict another embodiment of a vessel of the present invention that has been implanted and wherein the scaffolding material is a cotton knit.
Figure 11B:
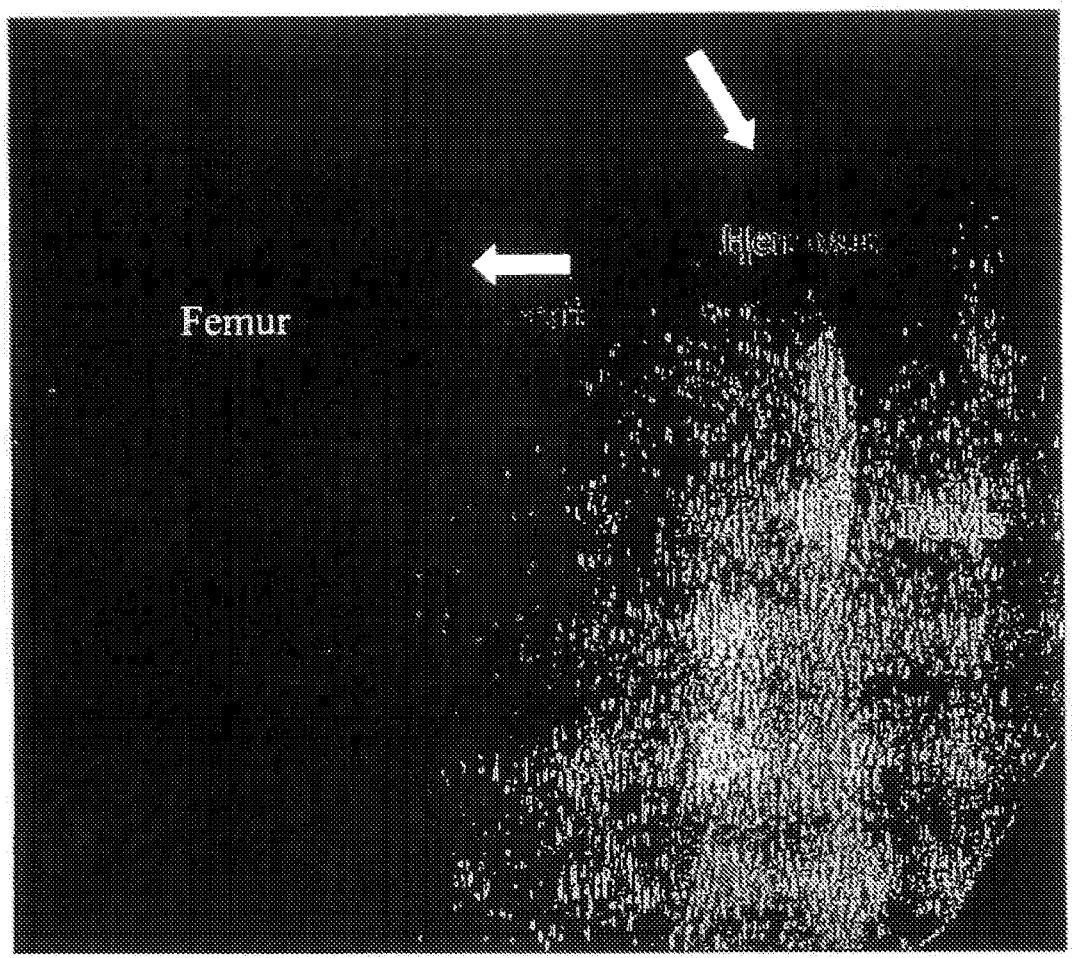

FIGS. 10A-B depict magnified cross-sectional views of one embodiment of a vessel of the present invention wherein the interior layer of a polyurethane foam tube adjacent to the lumen is predominately comprised of biocoacervate or biomaterial, the middle layer of the vessel includes an coacervate or biomaterial impregnated within a polyurethane foam and the exterior layer of the vessel is comprised of biocoacervate or biomaterial. FIG. 11A depicts another embodiment of a vessel graft implanted in a pig wherein the structural scaffolding of the vessel graft is a cotton knit material coated with another embodiment of a crosslinked biocoacervate material of the present invention. FIG. 11B is the angiogram image of the same vessel depicted in FIG. 11A after being implanted for nine days showing that the vessel graft remains patent. Histology showed after thirty days that the blood vessel graft did not clot blood and did not allow platelet attachment or any thrombosis. It was also found that smooth muscle cells and microvasculature were remodeling the crosslinked biocoacervated material.

The melted biocoacervate may be applied to the scaffolding structure, such as a polyurethane or cotton knit tube, by any process known in the art such as painting, injection molding, dip coating, spraying and the like. Furthermore, a scaffolding tubular structure may be strengthened by applying one or more rings of biocompatible polymer, such as Dacron to prevent tearing or crimping of the tubular graft ends. Alternatively, any materials including those identified above may be coated with the biocoacervate of the present invention utilizing the same process as described in the previous few sentences.

Figure 12A:
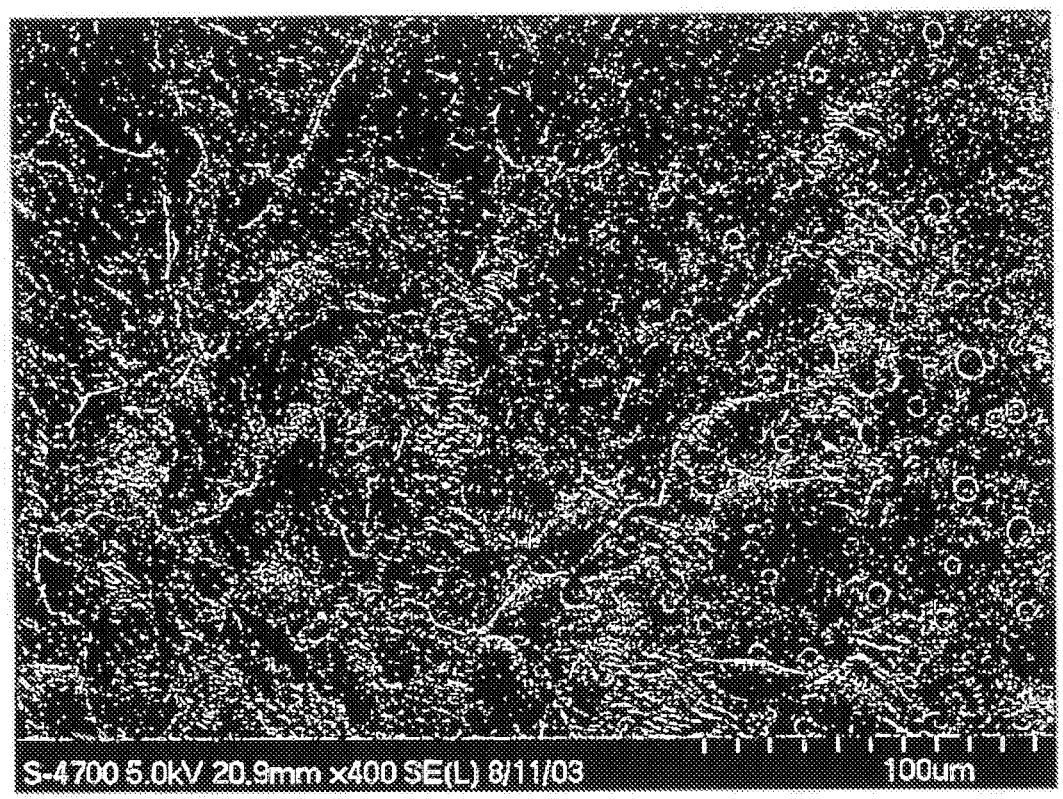
FIG. 12A-B depicts an embodiment of a tube made of the biomaterial of the present invention wherein endothelial cells are present on the surface of the biomaterial.
Figure 12B:
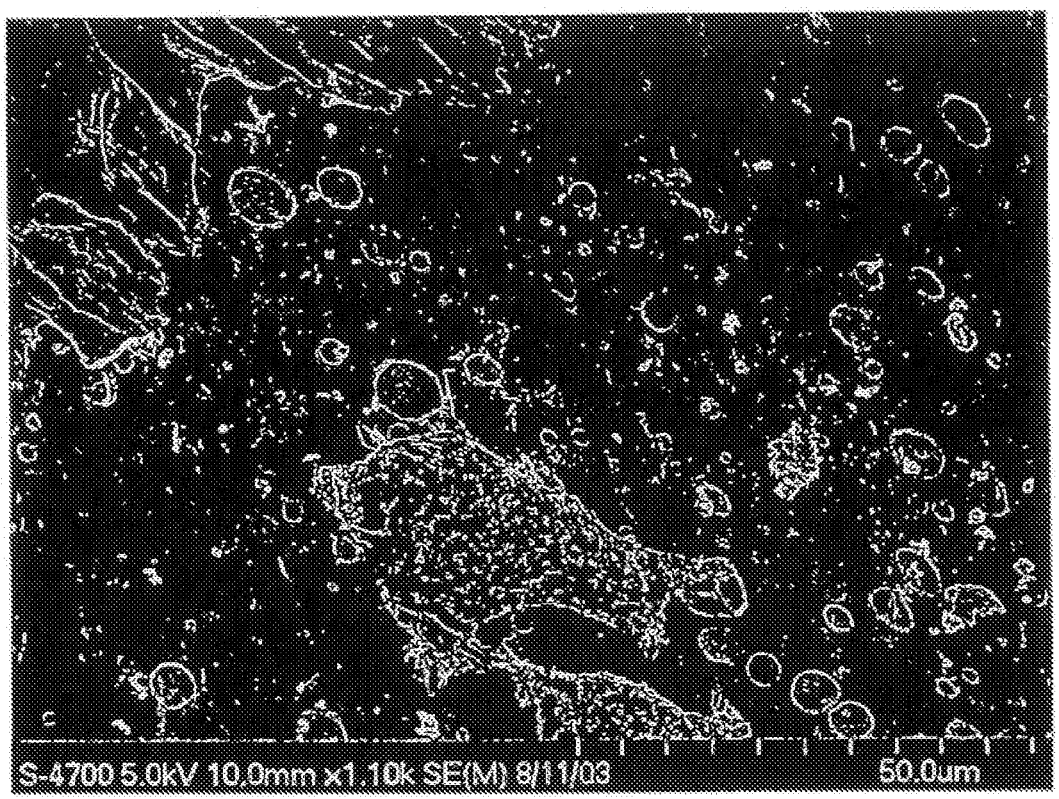

In view of such scaffolding structures, vessels and tubular grafts may be synthesized utilizing the biocoacervate and/or biomaterial. Generally, a vessel is a tubular graft made of the coacervates or biomaterials that can support the growth of cells on and/or within the coacervate or biomaterial. For example, vessels may be produced utilizing the coacervates or biomaterials that have the affinity to support growth of endothelial cells on the inside of the tube and smooth muscle cells on the outside of the tube. Furthermore, tubular grafts including such biocoacervates and biomaterials tend to have beneficial hemocompatible characteristics. FIG. 12A-B depicts various embodiments of tubes made of the biomaterial of the present invention wherein endothelial cells are present on the surface of the biomaterial. Alternatively, a multi-layered vessel may be created with two or more separate tubes, wherein a smaller tube with endothelial cells grown on the inside of the tube is inserted into a larger tube with smooth muscle cells grown on the outside of the tube. Additional tubular layers may be included in the vessel that may or may not include the growth of cells on the surfaces or within the coacervates or biomaterials. The layers may also contain pharmacologically active agents and/or more structural components, such as polymeric materials, knitted materials or stents. The layers will generally stay in position through adhesives, fasteners like sutures, melted biocoacervate solvent welding, cell interaction, pressure fitting, crosslinking, intermolecular forces and other layer alignment means and may adhere or may not adhere to each other. It is also noted that layers that include cell growth may also include pharmacologically active agents.

Once prepared the tubular graft or vessel may be administered to the patient as a replacement to a damaged vessel or as a scaffolding device that can be inserted into or mounted around the damaged vessel. Vascular tubes, known as a STUNT (Support Tube Using New Technology) can be used for placement within a blood vessel. Embodiments of the tubular grafts have form memory and will reform if cut or severed back to its original form and shape. A vessel structure of the present invention will meet the mechanical and histological requirements of a blood vessel, while providing the biological and biochemical functions that are necessary for its success. One embodiment that ensures mechanical integrity and biological compatibility is a scaffold comprising collagen, elastin and heparin. These proteins are the primary components of a typical arterial wall. This will create the natural environment for the endothelial cells, while providing the structural characteristics of these proteins. Endothelialization of the cylindrical matrices will provide the critical hemocompatibility, while also providing the thrombolytic characteristics. This feature will allow for the creation of small-diameter vascular grafts with a reduction in thrombosis. Embodiments of the tubular structure will have a diameter of approximately 2-4 mm due to the small-diameters of native coronary arteries. However, the tubular structure could be any size. Due to the prevalence of coronary disease and the need for effective treatments, the proposed tubular structure would be embraced as a compatible vascular graft.

Additionally, since the vessels or tubular grafts of the present invention are produced with a biocompatible protein and may include the growth of cells from the patient or compatible cells, the vessel or tubular graft administered to the host tissue further enhances acceptance and remodeling of the vessel or tubular graft by the host tissue. It is again noted that a benefit of the coacervates or biomaterials of the present invention is the modifying, adapting and/or transforming of the device into an interwoven and/or functioning part of the host tissue.

Furthermore, the vessels and/or tubular grafts may also include one or more pharmacologically active agents within or attached to the coacervates or biomaterials that may assist in the facilitation of tissue acceptance and remodeling, as well as inhibit additional adverse conditions sometimes related to implantation of vessels, such as platelet aggregation, cell proliferation and/or angiogenesis activity, all of which may cause blockage of the vessel. In addition to antiplatelet aggregation drugs, anti-inflammatory agent, gene altering agents, angiogenesis inhibitors, antiproliferative agents, enzymes, growth factors and other additional pharmacologically active agents can be included in the vessel and/or tubular graft for localized administration to or near the host tissue.

Figure 13:
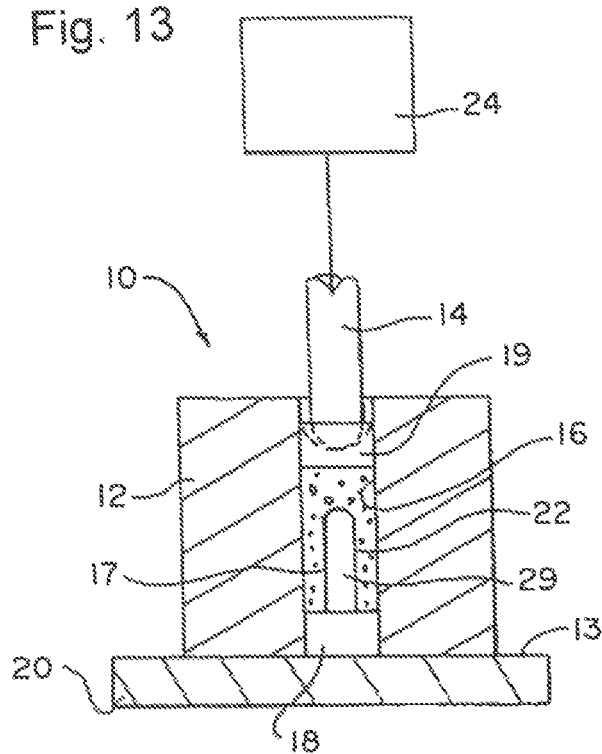
FIG. 13 depicts an embodiment of a compression molding device wherein the inner insert includes a mandrel.
Figure 14:
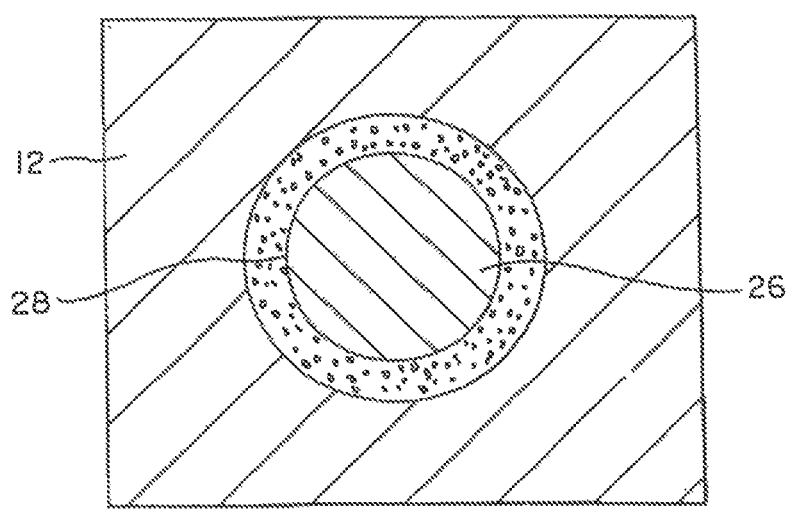
FIG. 14 depicts the top view of an embodiment of the compression molding device without the upper insert or plunger.

Embodiments of the biocoacervate or biomaterial vessels and/or tubular grafts may be prepared by methods similar to those described and suggested above. FIGS. 13 and 14 depict a compression molding device wherein the inner insert 18 includes a mandrel 29 that extends upward from the insert 18 into the chamber 17. FIG. 14 depicts a top view of the compression molding device without the upper insert 19 or plunger 14. Following the insertion of a sufficient amount of melted coacervate 22 the upper insert 19 and plunger 14 are applied to the coacervate 22. Once cooled, the vessel and/or tubular graft is then removed from the compression molding device and the vessel or graft is set utilizing a crosslinking technique. The vessel and/or tubular graft generally has a wall thickness of approximately 0.05 mm to 1 cm and preferably has a wall thickness of 0.15 to 1.5 mm.

Figure 15:
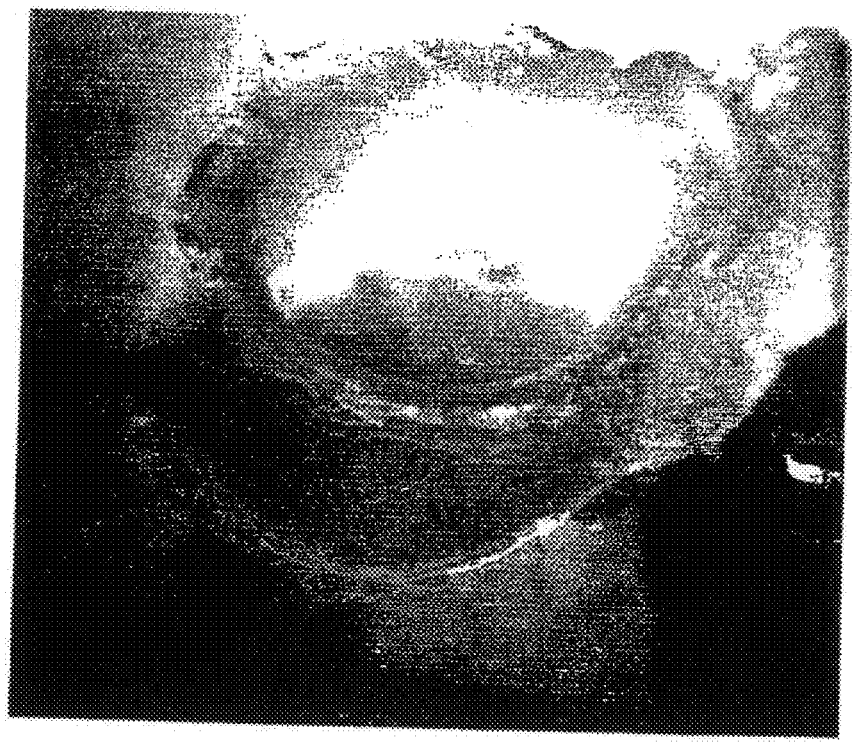
FIG. 15 depicts one embodiment of a vessel prepared by compressing particles of collagen/elastin/heparin and allowing the compressed particles to dry thereby setting the tublar configuration.

In an alternative embodiment, a vessel is prepared by compressing particles of the present invention into a tubular formation and allowing the formed tube to dry, thereby setting the structure. FIG. 15 depicts a vessel prepared by compressing particles of collagen/elastin/heparin and allowing the compressed particles to dry thereby setting the tublar configuration.

Furthermore, other tissue grafts may be made by including in the compression molding device a cavity 16 and inserts 18 and 19 that are configured to produce the size and shape of the tissue graft desired. For example valves such as heart valves; bone; cartilage; tendons; ligaments skin; pancreatic implant devices; and other types of repairs for tissue that relate to the heart, brain, abdomen, breast, palate, nerve, spinal cord, nasal, liver, muscle, thyroid, adrenal, pancreas, and surrounding tissue such as connective tissue, pericardium and peritoneum may be produced by forming the cavity 16 and inserts 18 and 19 of the molding compression chamber into the corresponding size and shape of the particular tissue part. Finally, the tissue grafts may be set by utilizing one or more crosslinking techniques as disclosed or suggested above. It is noted, that the above mentioned vessels and/or tissue grafts may optionally include one or more pharmacologically active agents or other structural additives, such as metal, insoluble proteins, polymeric and/or biocompatible materials including wire, ceramic, nylon, cotton or polymeric meshes or foams, especially foam, polymer, cotton or fiber tubes.

In another embodiment of the present invention, a containment or fixation device may be prepared utilizing sheets and/or particles, which include the biocoacervate or biomaterials of the present invention. Such containment or fixation devices are generally utilized to assist in the healing of broken bones, torn tendons, damaged vessels, spinal cord injury and the like. Examples of such fixation devices are disclosed or suggested in International Application No. PCT/US03/13273, the entire contents of which are incorporated by reference herein.

Wound Healing Devices:

Other embodiments of the present invention include wound healing devices that utilize the coacervates or biomaterials of the present invention. The wound healing devices may be configured in any shape and size to accommodate a wound being treated. Moreover, the wound healing devices of the present invention may be produced in whatever shape and size is necessary to provide optimum treatment to the wound. These devices can be produced in the forms that include, but are not limited to, plugs, meshes, strips, sutures, or any other form able to accommodate and assist in the repair of a wound. The damaged portions of the patient that may be treated with a device made of the coacervates or biomaterials of the present invention include skin, tissue (nerve, brain, spinal cord, heart, lung, etc.) and bone. Moreover, the wound healing device of the present invention may be configured and formed into devices that include, but are not limited to, dental plugs and inserts, skin dressings and bandages, bone inserts, tissue plugs and inserts, vertebrae, vertebral discs, joints (e.g., finger, toe, knee, hip, elbow, wrist,), tissue plugs to close off airway, (e.g., bronchial airway from resected tissue site), other similar devices administered to assist in the treatment repair and remodeling of the damaged tissue and/or bone.

In one embodiment of the wound healing device of the present invention, a coacervate or biomaterial may be formed into a dressing or bandage to be applied to a wound that has penetrated the skin. An example of an ultra-thin collagen/elastin/heparin biomaterial may be approximately 0.1 mm in thickness. Generally, the coacervates or biomaterials formed into a thin dressing or bandage may be approximately 0.05-10 mm in thickness, in a number of embodiments 1-2 mm.

The coacervate or biomaterial wound healing devices, upon application, adhere to the skin and will remain for days depending upon the conditions. If protected, embodiments of the coacervate or biomaterial dressing will remain on the skin for a considerable period of time. Moreover, if the coacervate or biomaterial is acting as a wound dressing and therefore interacting with a wound it will stick very tightly. The coacervates or biomaterials of the present invention may also act as an adhesive when wet. It is also noted that the coacervates or biomaterials of the present invention incorporated into a wound dressing would help facilitate or lessen scarring by helping to close the wound. Furthermore, coacervate or biomaterial dressings or bandages may be prepared to administer beneficially healing and repairing pharmacologically active agents, as well as, act as a device that may be incorporated and remodeled into the repairing tissue of the wound.

Figure 16:
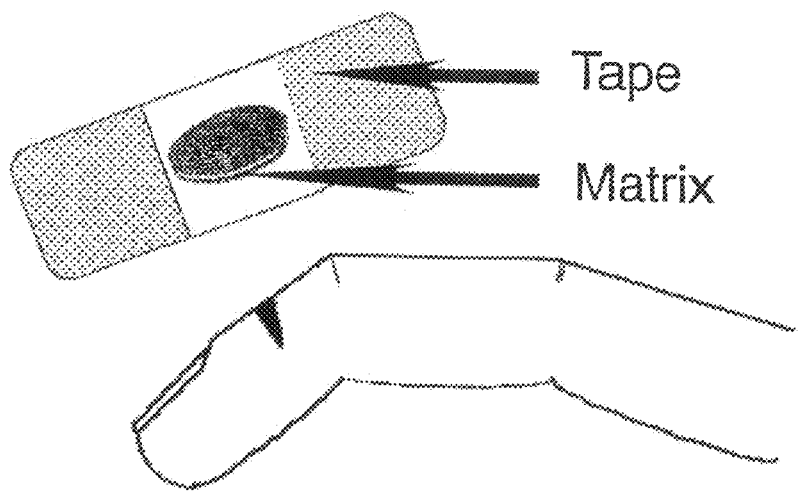
FIG. 16 depicts an embodiment of a wound healing device comprising a protein matrix that is positioned in the center of a non-adhesive strip of material attached to two adhesive ends.

In another embodiment of the present invention, the coacervates or biomaterials can also be protected with a tape barrier that is put over the coacervate or biomaterial and over the wound. A plastic and/or adhesive strip section of material may be used as a tape barrier that does not stick to the coacervate or biomaterial but holds it in place and provides more protection from the environment. Tape barriers that are utilized in bandages existing in the art, similar to bandages represented by the BANDAID® products, may be used with the dressing of the present invention. FIG. 16 depicts a wound dressing comprising a coacervate or biomaterial wound healing device that is positioned in the center of a non-adhesive strip of material attached to two adhesive ends.

Embodiments of the coacervate or biomaterial wound healing device, also provide a device wherein pharmacologically active agents can be included within or attached to the surface. The coacervates or biomaterials may include, but are not limited to, substances that help clotting, such as clotting factors, substances which are helpful for wound healing, such as vitamin E, as well as, anti-bacterial or anti-fungal agents to reduce the chance of infection. Other groups of pharmacologically active agents that may be delivered by the coacervates or biomaterials are analgesics, local anesthetics, other therapeutics to reduce pain, reduce scarring, reduce edema, and/or other type of drugs that would have very specific effects in the periphery and facilitate healing. Furthermore, the protein coacervate or biomaterial interacts with the cells that migrate to the wound to facilitate the healing process and that require a scaffolding and/or blood clotting before they can actually start working to close and remodel the wound area.

The coacervates or biomaterials of the present invention could also assist patients who require more assistance than normal for a wound to actually close. Individuals who have problems with wound healing may find that their wound takes longer to close due to their wound not being able to develop a clot and/or set up a structure for cells to close the wound. In these situations, such as a person with diabetes or ulcers, the coacervates or biomaterials of the present invention may be utilized to assist in healing. The coacervates or biomaterials provides a material that assists the wound in closing, especially if clotting factors, such as factor 14 and factor 8, and other similar biochemicals that are known in the art and are important to wound care are also added.

It is also possible to extend delivery of chemicals or drugs using the coacervate or biomaterial of the present invention in a layered wound dressing. In one embodiment this can be accomplished by providing wound dressing that includes a patch delivery system adjoined immediately behind a layer of the coacervate or biomaterial. In this example a strip, wrap or patch that includes a larger dosage of the chemical or pharmaceutical active component may be applied behind the coacervate or biomaterial, but not in immediate contact with the wound. By administering such a wound healing device, the delivery of chemicals and/or pharmaceuticals could be extended until the wound was healed or the desired amount of chemicals and/or pharmaceuticals were applied. In application, the layer of coacervate or biomaterial would continue to absorb more chemicals and/or pharmaceuticals from the patch as the initial material impregnated in the coacervate or biomaterial was being utilized in the wound. Therefore, the coacervate or biomaterial would provide a controlled release of the chemical and/or pharmaceutical component and would prevent the administration of too much chemical and/or pharmaceutical component from entering a patient's wound prematurely. Additionally, the coacervate or biomaterial with adjoining patch may be very beneficial for patients who are compromised in some way from internally supplying the biological substances needed to reduce or prevent them from healing quickly. Examples of such situations where such a coacervate or biomaterial wound healing device would be beneficial are in cases of diabetes, hemophilia, other clotting problems or any other type affliction that inhibits the adequate healing of a wound.

Additionally, embodiments of a coacervate or biomaterial dressing that includes a patch may be configured to allow a varying controlled release of pharmaceuticals through the coacervate or biomaterial by providing a layer system that release molecules at varying rates based on molecule size. This provides a tremendous means for controlling administration of more than one pharmacologically active agent that vary in size. Such controlled release facilitates the administration of pharmaceutical molecules into the wound when they may be needed. For example, the coacervate or biomaterial dressing may be layered with different types of protein material and biocompatible polymeric material mixtures that control the release of molecules based on size. For example, each layer of coacervate or biomaterial may include physical and/or chemical restraints that slow the migration of various size molecules from the patch and through the coacervate or biomaterial. Furthermore, the larger molecules that are proteins and other macromolecules that need to be in contact with the wound can be impregnated into the coacervate or biomaterial itself.

Figure 17:
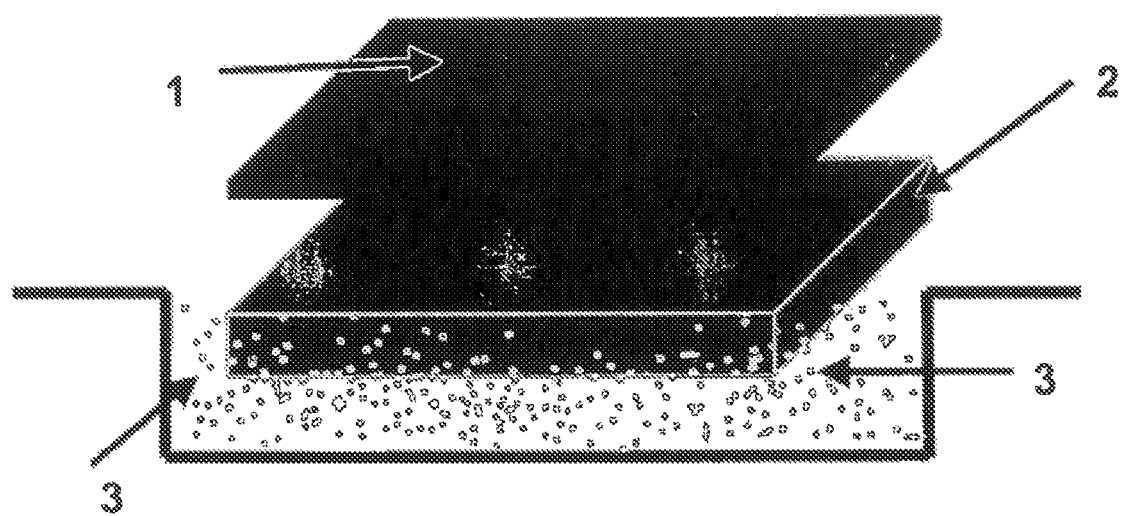
FIG. 17 depicts an embodiment of a bilaminar dressing that includes an Epithelial Cell Migration layer, a Fibroblast/Endothelial Infiltration layer and particles.

In an alternative wound healing device, as depicted in FIG. 17, a bilaminar dressing may include a an Epithelial Cell Migration layer and a Fibroblast/Endothelial Infiltration layer. Particles of the present invention may be placed into the wound prior to application of the laminar dressings to fill in the rough surface of the wound and optionally deliver pharmacologically active agents. Embodiments similar to these laminar wound healing dressings may assist to retain particles in the wound, thereby facilitating enhanced healing characteristics. It is noted that the embodiment depicted in FIG. 17 illustrate the layers of the bilaminated device interacting with keritinocytes (K), fibroblasts (F) and endothelial cells (E).

Furthermore, the coacervate or biomaterial may be set up with pores that allow fluid flow through that coacervate or biomaterial and also enhances movement of the pharmacologically active agents through the coacervate or biomaterial. Pores may be created in the coacervate or biomaterial by incorporating a substance in the coacervate or biomaterial during its preparation that may be removed or dissolved out of the coacervate or biomaterial before administration of the device or shortly after administration. Porosity may be produced in a coacervate or biomaterial by the utilization of materials such as, but not limited to, salts such as NaCl, amino acids such as glutamine, microorganisms, enzymes, copolymers or other materials, which will be leeched out of the coacervate or biomaterial to create pores. Other functions of porosity are that the pores create leakage so that cells outside the coacervate or biomaterial can receive fluids that include the contents of the coacervate or biomaterial and also that cells may enter the coacervate or biomaterial to interact and remodel the coacervate or biomaterial to better incorporate and function within the host tissue.

Alternatively, it is also possible to produce a porous coacervate or biomaterial by the incorporation of a solution saturated or supersaturated with a gaseous substance, such as carbon dioxide. In one embodiment, carbonated water may be utilized in a sealed and pressurized environment during the production of the coacervate or biomaterial or administered when the coacervate is in a melted state. The utilization of carbonated water creates bubbles within the coacervate or biomaterial during the production process or when administered in the melted state. Once the coacervate or biomaterial has been solidified, shaped into the desired form and removed from the sealed and pressurized environment, the gaseous bubbles escape from the coacervate or biomaterial leaving a porous material. In other embodiments, the pores can be produced by introducing gases, such as air, nitrogen, and the like, via whipping, bubbling, emulsifying, into the melted coacervate to create pores, which remain in the material after cooling and reformation. For example air or nitrogen may be bubbled or whipped into the melted coacervate while cooling to form pores. This process can be performed at atmospheric pressure or under applied pressure.

It is noted that the methods of producing a porous material as described above may be utilized in any embodiment described in the present invention, such as drug delivery devices, tissue grafts and the like.

The coacervates or biomaterials of the present invention may also be utilized as port seals for protrusion devices entering and or exiting the patient. FIG. 18 depicts one embodiment of a protrusion device 34 that includes a port seal 36 comprising a coacervate or biomaterial of the present invention. The port seal 26 may be included around the point of insertion of a protrusion device, such as an electrical lead, a drug delivery needle or a catheter. Generally, the port seal 36 surrounds the protrusion device 34 and insulates it from the host tissue. One or more tabs 38 may optionally be included on the port seal 36 to assist in the retention of the protrusion device and further seal the opening in the patients skin. The tabs 38 may be inserted under the skin or may remain on the outside of the patient's skin. Also, the biocompatible seal comprising the coacervate or biomaterial of the present invention provides stability, reduces the seeping of bodily fluid from around the protrusion and reduces or prevents immunogenicity caused by the protrusion device. Furthermore, the port seal may include pharmacologically active agents that may be included to deliver anti-bacterial, analgesic, anti-inflammatory and/or other beneficial pharmacologically active agents.

Other embodiments of the present invention include coacervates or biomaterials configured and produced as biological fasteners, such as threads, adhesives, sutures and woven sheets. Threads, adhesives and sutures comprising various embodiments of the coacervate or biomaterial provide a biocompatible fastening, adhering and suturing function for temporarily treating and sealing an open wound. Additionally, the biological fasteners may include pharmacologically active agents that may assist in the healing and remodeling of the tissue within and around the wound.

One method of preparing the biocompatible biological fasteners is to manufacture sheets of coacervate or biomaterial. Once the sheets of coacervate or biomaterial are prepared, each sheet may be cut into strips, threads or other shapes to form sutures, threads and other biological fasteners (e.g., hemostats). The sheets may be cut using cutting techniques known in the art. Also, the coacervate or biomaterial threads may be woven into sheets and used as strengthened biomaterial weaves that has desired porosity.

Additionally, fibers (large or small, e.g., macro, micro, nano) of a known suturing material, such as nylon, may be incorporated in the coacervate or biomaterial when making a sheet of the biomaterial. Once the sheet is prepared it may be cut by methods common to the art to produce a thread/suture that has biocompatible and durable characteristics.

Additional embodiments of wound healing devices that include the coacervate or biomaterial of the present invention include but are not limited to dental inserts, dental plugs, dental implants, dental adhesives, denture adhesives or liners and other devices utilized for dental applications. Wounds and dental complications, such as dry socket, present within the interior of the mouth are generally slow to heal, are painful and/or are susceptible to bacterial and other forms of infection.

The dental inserts or implants of the present invention may be utilized to remedy such problems since they are biocompatible with the surrounding host tissue and may be manufactured to release appropriate pharmacologically active agents that may assist in healing, relieve pain and/or reduce bacterial attack of the damaged region. Furthermore, the dental plugs, inserts or implants produced with the coacervates or biomaterials of the present invention may be incorporated into and remodeled by the surrounding tissue, thereby hastening the healing of the damaged region and/or returning the damaged region to its original state. For example, dental plugs or implants including the coacervates or biomaterials of the present invention may be administered to open wounds within the mouth region of the patient following tooth extraction, oral surgery or any other type of injury to the interior of the mouth to assist in the healing and regeneration of the damaged region.

In general, the dental plugs, implants or inserts may be administered to the damaged area by any method known in the art. For example a dental plug may be administered to the socket of a tooth after removal by placing a properly sized and shaped dental plug that includes the coacervate or biomaterial of the present invention into the socket. The dental plug may optionally be fastened to the surrounding tissue of the socket by any means known in the art such as adhesives or sutures. However, it may not be necessary to use any fastening means since the cells of the host tissue may be found to readily interact with the plug and begin to incorporate the plug into the host tissue. As previously suggested, such a dental plug may also include analgesic antibacterial, and other pharmacologically active agents to reduce or prevent pain and infection and to promote the reconstruction of the damaged region.

EXAMPLES

The biomaterials and biocoacervates of the present invention will now be further described with reference to the following non-limiting examples and the following materials and methods that were employed.

Example 1

Preparation of Biocoacervate

Soluble bovine collagen (Kensey-Nash Corporation) (1.5 gs) was dissolved in distilled water (100 mls) at 42° C. To this solution was added elastin (bovine neck ligament, 0.40 g) and sodium heparinate (0.20 g) dissolved in distilled water (40 mls) at room temperature. The elastin/heparin solution was added quickly to the collagen solution with minimal stirring thereby immediately producing an amorphous coacervate precipitate. The resulting cloudy mixture was let standing at room temperature for 1-2 hrs and then refrigerated. The rubbery precipitate on the bottom of the reaction flask was rinsed three times with fresh distilled water and removed and patted dry with filter paper to yield 6.48 gs of crude coacervate (MELGEL™) which was then melted at 55° C. and gently mixed to yield a uniform, rubbery, water-insoluble final product after cooling to room temperature. The supernatant of the reaction mixture was later dried down to a solid which weighed 0.417 g and was water soluble. The uniform MELGEL™ material was used to fabricate both injectable compositions for tissue augmentation and biocompatible structures for vascular grafts.

Example 2

Biocoacervate Materials Including Additives and pH Solutions

MELGEL™ material was prepared as described in Example 1. Nine 1 g samples of MelGel™ were cut and placed in a glass scintillation vial. The vial was then placed in a water bath at 60° C. and melted. Once melted either an additive or pH solution was added to each sample of MELGEL™. The following additives were administered: polyethylene glycol, chondroitin sulfate, hydroxyapatite, glycerol, hyaluronic acid and a solution of NaOH. Each of the above mentioned additives were administered at an amount of 3.3 mg separately to four melted samples of MELGEL™ with a few drops of water to maintain MELGEL™ viscosity during mixing. Each of the above mentioned additives were also administered at an amount of 10 mg to another four melted samples of MELGEL™ with a few drops of water to maintain MELGEL™ viscosity. Finally, NaOH was added to the final melted MELGEL™ sample until the MELGEL™ tested neutral with pH indicator paper. The uniform MELGEL™ material including additives or pH solution were crosslinked with 0.1% gluteraldehyde for 2 hours and used to fabricate injectable compositions for tissue augmentation.

Example 3

Preparation of Ground Particles

A sample of MELGEL™ was cut into small pieces and treated with a glutaraldehyde (0.1-1.0%) aqueous solution for up to 2 hours. The resulting coacervate (MELGEL™) material was then dried at 45° C. for 24 hours and ground to a fine powder and sieved through a 150µ screen. This powder was then suspended in phosphate-buffered saline to give a thick, flowable gel-like material which could be injected through a fine needle (23-30 ga.). This formulation is useful for augmentation of facial wrinkles after intradermal injection.

Example 4

Preparation of Homogenized Particles

Samples of MELGEL™ as described in Example 2 were cut into small pieces and treated with a glutaraldehyde (0.1%) aqueous solution for 2 hours, was rinsed three times with distilled water, treated with a glycine/glutamine solution for 30 minutes and rinsed again twice with distilled water. It is noted that other embodiments have been treated with 0.2, 0.5 and 1% gluteraldehyde solutions to crosslink the MELGEL™. The material was next placed in PBS overnight. The crosslinked coacervate (MELGEL™) material was removed from PBS solution and homogenized with a handheld homogenizing polytron to form a wet viscous fine particle mass. The viscous particle mass was then loaded into syringes, which could be injected through a fine needle (23-30 ga.). This formulation is useful for augmentation of facial wrinkles after intradermal injection.

Example 5

Preparation of a Vascular Graft

A open-cell polyurethane foam tube was fabricated with an outside diameter of 6 mm and a wall thickness of 1 mm. This tube was placed into a container with sufficient coacervate (MELGEL™) in the melted state to completely cover the tube. This combination was placed into a vacuum oven held at 55° C. and a vacuum pulled until trapped air in the polyurethane tube was removed. The vacuum was released and the MELGEL™ impregnated tube was cooled to room temperature and placed into distilled water followed by immersion in a 0.1% aqueous solution of glutaraldehyde for 2 hours. The resulting tubular graft was then suitable for use as a replacement vessel graft after appropriate sterilization.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

---

The invention claimed is:

1. A method of treating a wound comprising administering to the wound a biomaterial comprising an amorphous material that is crosslinked with one or more crosslinking agents, the amorphous material including aggregated complexes having homogenously distributed biocoacervated components, the components comprising one or more soluble or solubilized primary proteins combined with one or more glycosaminoglycans and one or more biocompatible solvents.

2. The method of treating a wound of claim 1 wherein the biomaterial further comprises one or more pharmacologically active agents.

3. The method of treating a wound of claim 2 wherein the one or more pharmacologically active agents are selected from the group consisting of analgesics, anesthetics, antiproliferative agents, angiogenesis inhibitors, antipsychotic agents, angiogenic growth factors, bone mending biochemicals, steroids, antisteroids, corticosteroids, antiglacoma agents, antialcohol agents, anti-coagulant agents, genetic material, antithrombolytic agents, anticancer agents, anti-Parkinson agents, antiepileptic agents, anti-inflammatory agents, anticonception agents, enzymes agents, cells, growth factors, antiviral agents, antibacterial agents, antifungal agents, hypoglycemic agents, antihistamine agents, chemoattractants, neutraceuticals, antiobesity, smoking cessation agents, obstetric agents and antiasmatic agents.

4. The method of treating a wound of claim 1 further comprising one or more secondary proteins.

5. The method of treating a wound of claim 4 wherein the one or more secondary proteins are selected from the group consisting of fibrin, fibrinogen, elastin, albumin, ovalbumin, keratin, silk, silk fibroin, actin, myosin, thrombin, aprotinin and antithrombin III.

6. The method of treating a wound of claim 1 wherein the one or more biocompatible solvents are selected from the group consisting of water, dimethyl sulfoxide (DMSO), biocompatible alcohols, biocompatible acids, oils and biocompatible glycols.

7. The method of treating a wound of claim 1 further comprising one or more biocompatible additives.

8. The method of treating a wound of claim 7 wherein the one or more biocompatible additives are selected from the group consisting of epoxies, polyesters, acrylics, nylons, silicones, polyanhydride, polyurethane, polycarbonate, poly(tetrafluoroethylene), polycaprolactone, polyalkenes, polyacrylates, bioceramic materials, polyethylene oxide, polyethylene glycol, poly(vinyl chloride), polylactic acid, polyglycolic acid, polypropylene oxide, poly(alkylene)glycol, polyoxyethylene, sebacic acid, polyvinyl alcohol, 2-hydroxyethyl methacrylate, polymethyl methacrylate, 1,3-bis(carboxyphenoxy)propane, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly(amido amines), glycosaminoglycans, bioceramic materials, insoluble proteins, proteins, amino acids, oils, fatty acids, salts, sugars, polypeptides, peptides, humectants, fibrin, graphite, flexible fluoropolymer, isobutyl-based, isopropyl styrene, vinyl pyrrolidone, cellulose acetate dibutyrate, silicone rubber, and copolymers of these.

9. The method of treating a wound of claim 8 wherein the one or more additives are selected from the group consisting of hyaluronic acid, chondroitin sulfate, hydroxyapatite, polyethylene glycol, glycerol, sodium hydroxide and potassium hydroxide.

10. The method of treating a wound of claim 1 wherein the one or more crosslinking agents are selected from the group consisting of glutaraldehyde, 1,4-butandiol diglycidylether, formaldehyde, glyoxal, sebacic acid bis(N-succinimidyl)ester (DSS), p-Azidobenzolyl Hydazide, N-5-Azido 2-nitrobenzoyloxysuccinimide, N-Succinimidyl 6-[4'azido-2'nitro-phenylamino]hexanoate and 4-[p-Azidosalicylamido]butylamine.

11. The method of treating a wound of claim 1 wherein the biomaterial is administered to a wound in one or more forms selected from the group consisting of a cylinder, wafer, bar, sphere, capsule, vessel, tubular graft, particles, biomesh, plug, sheet and valve.

12. The method of treating a wound of claim 1 wherein the one or more glycosaminoglycans are selected from the group consisting of heparin, heparin sulfate, keratan sulfate, dermatin, dermatin sulfate, heparin-hyaluronic acid, chondroitin, chondroitin sulfate, chondroitin 6-sulfate, chondroitin 4-sulfate, chitin, chitosan, acetyl-glucosamine, hyaluronic acid, aggrecan, decorin, biglycan, fibromodulin, lumican and complexes thereof.

* * * * *

SEQUENCE LISTING

<160> NUMBER OF SEQ ID NOS: 21

<210> SEQ ID NO 1
<211> LENGTH: 59
<212> TYPE: PRT
<213> ORGANISM: Artificial
<220> FEATURE:
<223> OTHER INFORMATION: synthetic construct similar to silk protein

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

```
Gly Ala Gly Ser Gly Ala Gly Ala Gly Ser Gly Ala Gly Ala Gly Ser
        35                  40                  45

Gly Ala Gly Ala Gly Ser Gly Ala Ala Gly Tyr
        50                  55

<210> SEQ ID NO 2
<211> LENGTH: 6
<212> TYPE: PRT
<213> ORGANISM: Artificial
<220> FEATURE:
<223> OTHER INFORMATION: seq. repeated indefinitely, synthetic
      construct similar to silk protein

<400> SEQUENCE: 2

Gly Ala Gly Ala Gly Ser
1               5

<210> SEQ ID NO 3
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing RGD sequence from fibronectin.

<400> SEQUENCE: 3

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Val Thr Gly Arg Gly Asp Ser
        50                  55                  60

Pro Ala Ser Ala Ala Gly Tyr
65                  70

<210> SEQ ID NO 4
<211> LENGTH: 74
<212> TYPE: PRT
<213> ORGANISM: Artificial
<220> FEATURE:
<223> OTHER INFORMATION: seq. repeated indefinitely, synthetic construct
      similar to silk protein containing sequence from laminin protein.

<400> SEQUENCE: 4

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
        50                  55                  60

Ala Val Ser Ala Gly Pro Ser Ala Gly Tyr
65                  70

<210> SEQ ID NO 5
<211> LENGTH: 73
<212> TYPE: PRT
<213> ORGANISM: Artificial
```

```
<220> FEATURE:
<223> OTHER INFORMATION: seq. repeated indefinitely, synthetic construct
      similar to silk protein containing a different sequence from
      laminin protein.

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Gly Pro Ser Ala Gly Tyr
65                  70

<210> SEQ ID NO 6
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing the RGD sequence from fib
      ronectin.

<400> SEQUENCE: 6

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Arg Tyr Val Val Leu Pro Arg Pro Val Cys
    50                  55                  60

Phe Glu Lys Ala Ala Gly Tyr
65                  70

<210> SEQ ID NO 7
<211> LENGTH: 20
<212> TYPE: PRT
<213> ORGANISM: Artificial
<220> FEATURE:
<223> OTHER INFORMATION: seq. repeated indefinitely, synthetic construct
      similar to elastin protein.

<400> SEQUENCE: 7

Val Pro Gly Val Gly Val Pro Gly Val Gly Val Pro Gly Val Gly Val
1               5                   10                  15

Pro Gly Val Gly
            20

<210> SEQ ID NO 8
<211> LENGTH: 52
<212> TYPE: PRT
<213> ORGANISM: Artificial
<220> FEATURE:
<223> OTHER INFORMATION: seq. repeated indefinitely, synthetic construct
      similar to silk and elastin proteins.
```

```
<400> SEQUENCE: 8

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Ala Gly Ala Gly Ser Gly Ala
            35                  40                  45

Gly Ala Gly Ser
        50

<210> SEQ ID NO 9
<211> LENGTH: 82
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 9

Gly Ala Ala Val Pro Gly Val Gly Val Pro Gly Val Gly Val Pro Gly
1               5                   10                  15

Val Gly Val Pro Gly Val Gly Val Ala Ala Gly Tyr Gly Ala Gly Ala
                20                  25                  30

Gly Ser Gly Ala Gly Ala Gly Ser Gly Ala Gly Ala Gly Ser Gly Ala
            35                  40                  45

Gly Ala Gly Ser Gly Ala Gly Ala Gly Ser Gly Ala Gly Ala Gly Ser
        50                  55                  60

Gly Ala Gly Ala Gly Ser Gly Ala Gly Ala Gly Ser Gly Ala Gly Ala
65                  70                  75                  80

Gly Ser

<210> SEQ ID NO 10
<211> LENGTH: 111
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 10

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Ala Gly Tyr Gly Ala Gly Ala Gly Ser Gly
            35                  40                  45

Ala Gly Ala Gly Ser Gly Ala Gly Ala Gly Ser Gly Ala Gly Ala Gly
        50                  55                  60

Ser Gly Ala Gly Ala Gly Ser Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro
                100                 105                 110
```

```
<210> SEQ ID NO 11
<211> LENGTH: 88
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 11

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser
                85

<210> SEQ ID NO 12
<211> LENGTH: 108
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 12

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
                85                  90                  95

Gly Ala Gly Ala Gly Ser Gly Ala Gly Ala Gly Ser
            100                 105

<210> SEQ ID NO 13
<211> LENGTH: 128
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 13

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30
```

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
 50                  55                  60

Pro Gly Val Gly Val Pro Gly Val Gly Val Pro Gly Val Gly Val Pro
 65                  70                  75                  80

Gly Ala Gly Ala Gly Ser Gly Ala Gly Ala Gly Ser Gly Ala Gly Ala
                 85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
            115                 120                 125

<210> SEQ ID NO 14
<211> LENGTH: 208
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 14

Gly Val Gly Val Pro Gly Val Gly Val Pro Gly Val Gly Val Pro Gly
 1               5                  10                  15

Val Gly Val Pro Gly Val Gly Val Pro Gly Val Gly Val Pro Gly Val
             20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
 50                  55                  60

Pro Gly Val Gly Val Pro Gly Val Gly Val Pro Gly Val Gly Val Pro
 65                  70                  75                  80

Gly Val Gly Val Pro Gly Val Gly Val Pro Gly Val Gly Val Pro Gly
                 85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
            115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Ala Gly Ala Gly Ser Gly Ala Gly Ala Gly Ser Gly Ala Gly Ala
                165                 170                 175

Gly Ser Gly Ala Gly Ala Gly Ser Gly Ala Gly Ala Gly Ser Gly Ala
            180                 185                 190

Gly Ala Gly Ser Gly Ala Gly Ala Gly Ser Gly Ala Gly Ala Gly Ser
            195                 200                 205

<210> SEQ ID NO 15
<211> LENGTH: 76
<212> TYPE: PRT
<213> ORGANISM: Artificial
<220> FEATURE:
<223> OTHER INFORMATION: seq. repeated indefinitely, synthetic construct
      similar to silk and elastin proteins.

```
<400> SEQUENCE: 15

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser
65                  70                  75

<210> SEQ ID NO 16
<211> LENGTH: 64
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 16

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

<210> SEQ ID NO 17
<211> LENGTH: 56
<212> TYPE: PRT
<213> ORGANISM: Artificial
<220> FEATURE:
<223> OTHER INFORMATION: seq. repeated indefinitely, synthetic construct
      similar to keratin protein.

<400> SEQUENCE: 17

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
            20                  25                  30

Leu Ala Glu Ala Lys Leu Glu Leu Ala Glu Ala Lys Leu Lys Leu Ala
        35                  40                  45

Glu Ala Lys Leu Glu Leu Ala Glu
    50                  55

<210> SEQ ID NO 18
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.
```

```
<400> SEQUENCE: 18

Gly Ala Pro Gly Pro Pro Gly Pro Pro Gly Pro Pro Gly Pro Pro
1               5                   10                  15

<210> SEQ ID NO 19
<211> LENGTH: 39
<212> TYPE: PRT
<213> ORGANISM: Artificial
<220> FEATURE:
<223> OTHER INFORMATION: seq. repeated indefinitely,  synthetic
      construct similar to collagen protein.

<400> SEQUENCE: 19

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro
        35

<210> SEQ ID NO 20
<211> LENGTH: 63
<212> TYPE: PRT
<213> ORGANISM: Artificial
<220> FEATURE:
<223> OTHER INFORMATION: seq. repeated indefinitely, synthetic construct
      similar to collagen protein with a cell binding domain from
      human collagen.

<400> SEQUENCE: 20

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Lys Gly Ala Asp
        35                  40                  45

Gly Ser Pro Gly Pro Ala Gly Pro Ala Gly Pro Val Gly Ser Pro
    50                  55                  60

<210> SEQ ID NO 21
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 21

Gly Ala Pro Gly Ala Pro Gly Ser Gln Gly Ala Pro Gly Leu Gln
1               5                   10                  15
```